(12) United States Patent
Larsen

(10) Patent No.: US 11,352,625 B2
(45) Date of Patent: Jun. 7, 2022

(54) COMPOSITIONS AND METHODS FOR DISRUPTING THE MOLECULAR MECHANISMS ASSOCIATED WITH MITOCHONDRIAL DYSFUNCTION AND NEURODEGENERATIVE DISEASE

(71) Applicant: Duke University, Durham, NC (US)

(72) Inventor: Peter Anthony Larsen, Durham, NC (US)

(73) Assignee: DUKE UNIVERSITY, Durham, NC (US)

(*) Notice: Subject to any disclaimer, the term of this patent is extended or adjusted under 35 U.S.C. 154(b) by 119 days.

(21) Appl. No.: 16/477,645

(22) PCT Filed: Jan. 12, 2018

(86) PCT No.: PCT/US2018/013645
§ 371 (c)(1),
(2) Date: Jul. 12, 2019

(87) PCT Pub. No.: WO2018/132755
PCT Pub. Date: Jul. 19, 2018

(65) Prior Publication Data
US 2021/0155925 A1    May 27, 2021

Related U.S. Application Data

(60) Provisional application No. 62/468,146, filed on Mar. 7, 2017, provisional application No. 62/445,279, filed on Jan. 12, 2017.

(51) Int. Cl.
C12N 15/113     (2010.01)
C12N 15/63      (2006.01)
(Continued)

(52) U.S. Cl.
CPC .............. *C12N 15/113* (2013.01); *C12N 9/22* (2013.01); *C12Q 1/6883* (2013.01);
(Continued)

(58) Field of Classification Search
CPC .............. A61K 31/7088; C12N 15/113; C12N 2310/11; C12N 2310/20; C12N 2310/141; C12N 9/22
See application file for complete search history.

(56) References Cited

U.S. PATENT DOCUMENTS

2005/0266459 A1    12/2005    Poulsen et al.
2010/0183610 A1    6/2010     Li et al.
(Continued)

FOREIGN PATENT DOCUMENTS

WO    2006083854 A2    8/2006
WO    2017214471 A1    12/2017

OTHER PUBLICATIONS

NHS prevention Alzheimer's disease. Downloaded from Alzheimer's disease—Prevention—NHS (www.nhs.uk) on Aug. 23, 2021.*
(Continued)

*Primary Examiner* — Terra C Gibbs
(74) *Attorney, Agent, or Firm* — NK Patent Law

(57) ABSTRACT

Retrotransposons, operating though human-specific neurological pathways, can contribute to environment, lifestyle, and/or age-related neurodegeneration by disrupting functional mitochondrial populations within neurons. The mitochondrial disruption can occur through a number of retrotransposon-induced mechanisms that can influence the efficient and accurate transcription and/or translation of mitochondrial genes encoded in the nuclear genome, operating primarily through epigenetic processes. Alu element-related conformational changes (both subtle and major) of the outer and inner mitochondrial membrane pores can restrict or prevent the normal translocation of proteins (i.e., TOMM and TIMM complexes), ultimately contributing to mitochondrial stress, mitophagy, inflammation, and neuron and glial cell death. Compositions and methods are provided for mitigating and/or preventing Alu element-induced conformational changes to prevent and/or treat neurodegenerative disease and other diseases and disorders associated with at least one TOMM, TIMM, or APOE isoform including cancer and other inflammatory diseases.

4 Claims, 10 Drawing Sheets

Specification includes a Sequence Listing.

(51) Int. Cl.
   *A61K 9/127* (2006.01)
   *A61K 31/7088* (2006.01)
   *C12N 9/22* (2006.01)
   *C12Q 1/6883* (2018.01)

(52) U.S. Cl.
   CPC .... *C12N 2310/11* (2013.01); *C12N 2310/141* (2013.01); *C12N 2310/20* (2017.05); *C12Q 2600/154* (2013.01)

(56) References Cited

U.S. PATENT DOCUMENTS

2013/0164845 A1  6/2013  Polach et al.
   2015/0051212 A1  2/2015  Stern et al.
   2015/0073025 A1  3/2015  Roses
   2015/0141320 A1  5/2015  Krieg et al.

OTHER PUBLICATIONS

ISA/US; International Search Report and Written Opinion for International Patent Application No. PCT/US18/13645 dated May 10, 2018, 17 pages.

De Andrade, A. et al., "Genetic and epigenetic variations contributed by Alu retrotransposition" BioMed Central Genomics, Dec. 20, 2011, vol. 12, No. 614; pp. 1-13.

WIPO, International Preliminary Report on Patentability for International Patent Application No. PCT/US2018/013645 dated Jul. 16, 2019.

* cited by examiner

MGNVLAASSPPAGPPPPPAPALVQLPPPPSPPGFTLPPLQGSLQAGTSTSRSSERTPQAATASASGAAEDGACQCLPNP

GTFEECHRKCKELFPIQMEGVKLTVNKGLSNHFQVNHTVALSTIGESNYHFGVTYVGTKQLSPTEAFPVLVGDMDNSGSL

NAQVIHQLGPGLRSKMAIQTQQSKFVNWQVDGEYRGSDFTAAVTLGNPDVLVGSGILVAHYLQSITPCLALGGELVYHRR

PGEEGTVMSLAGKYTLNNWLATVTLGQAGMHATYYHKASDQLQVGVEFEASTRMQDTSVSFGYQLPKANLLFKGSVDS

NWIVGATLEKKLPPLPLTLALGAFLNHRKNKFQCGFGLTIG

Normal Tom40

Tom40'

A.

B.

C.

COMPOSITIONS AND METHODS FOR DISRUPTING THE MOLECULAR MECHANISMS ASSOCIATED WITH MITOCHONDRIAL DYSFUNCTION AND NEURODEGENERATIVE DISEASE

RELATED APPLICATIONS

This application is a U.S. National Stage application of International Application No. PCT/US18/13645, filed on Jan. 12, 2018, which claims priority to U.S. Provisional Patent Application No. 62/445,279 filed on Jan. 12, 2017, and U.S. Provisional Patent Application No. 62/468,146 filed on Mar. 7, 2017, which are incorporated by reference herein in their entireties.

SEQUENCE LISTING

The instant application contains a Sequence Listing which has been submitted electronically in ASCII format and is hereby incorporated by reference in its entirety. Said ASCII copy, created on Dec. 28, 2021, is named 400_41_UTIL_SL.txt and is 35,050 bytes in size.

TECHNICAL FIELD

The presently disclosed subject matter is directed to compositions and methods of disrupting the molecular mechanisms associated with mitochondrial dysfunction that contribute to disease, including neurodegenerative disease.

BACKGROUND

A hallmark of human neurodegenerative disorders is the accumulation of protein aggregates (e.g., fibrils, tangles, amyloid plaques, Lewy bodies, inclusion bodies) in the brain. For example, clusters of amyloid precursor protein fragments are observed in patients with Alzheimer's Disease ("AD"). Further, alpha-synuclein molecules (i.e. Lewy Bodies) have been observed in patients with Parkinson's disease, and inclusion bodies in patients with amyotrophic lateral sclerosis (ALS), chronic traumatic encephalopathy (CTE), and Huntington's disease. Mitochondrial dysfunction is hypothesized to play a role in the initial intra-cellular formation of these neuronal protein aggregates and subsequent inflammation and neuronal damage associated with multiple neurological disorders. It would therefore be beneficial to provide a method of disrupting the molecular mechanisms that contribute to environmental, lifestyle, stress, and/or age-related dysfunctional mitochondrial populations to help prevent the incipient formation of inflammatory protein bodies the development and progression of neurodegenerative disorders.

DNA-RNA and RNA-RNA hybridization has been utilized in a range of technologies including for nucleic acid detection and for alteration of gene expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs). For example, an antisense drug, VITRAVENE (for treatment of cytomegalovirus retinitis), has been approved by the Federal Drug Administration, reflecting that antisense has therapeutic utility.

There remains a long standing unmet need for effective therapies to treat neurodegenerative diseases including Alzheimers Disease, and other diseases and disorders related to dysfunctional mitochondrial populations. The present invention provides such compositions and methods for the treatment of neurodegenerative disease and other diseases and disorders resulting from dysfunctional mitochondrial populations.

SUMMARY

In some embodiments, the presently disclosed subject matter is directed to a method of modulating the function, expression, or both of a TOMM, TIMM, or APOE isoform polynucleotide in the cells of a subject.

In some embodiments, the presently disclosed subject matter is directed to a method of preventing or treating a disease or disorder associated with at least one TOMM, TIMM, or APOE isoform. The disclosed method comprises administering to a subject a therapeutically effective dose of a composition comprising at least one antisense oligonucleotide that binds to a TOMM, TIMM, or APOE isoform polynucleotide, thereby preventing or treating the disease or disorder. In some embodiments, the disease or disorder is a neurological disorder, such as Alzheimer's disease, amyotrophic lateral sclerosis (ALS), chronic traumatic encephalopathy (CTE), or Parkinson's disease. In some embodiments, the antisense oligonucleotide is an antisense RNA molecule, an antisense DNA molecule, an interference RNA (RNAi), a micro RNA, a decoy RNA molecule, a siRNA, an enzymatic RNA, or a therapeutic editing RNA. In some embodiments, the antisense oligonucleotide has at least 50%, 75%, or 95% sequence identity to a reverse complement of the TOMM, TIMM, or APOE isoform polynucleotide. In some embodiments, the isoform is an Alu element-induced isoform, such as an Alu element-induced TOMM40 isoform. In some embodiments, the TOMM40 isoform comprises the target region set forth in SEQ ID NO:119. In some embodiments, the antisense oligonucleotide is selected from SEQ ID NOs:1-11. In some embodiments, the composition comprising the antisense oligonucleotide is administered intraventricularly, intranasally, intrathecally, or systemically to the subject. In some embodiments, the subject is a human.

In some embodiments, the presently disclosed subject matter is directed to a composition comprising one or more antisense oligonucleotides, wherein the antisense oligonucleotide has at least 50%, 75%, or 95% sequence identity to a reverse complement of a TOMM, TIMM, or APOE isoform polynucleotide. In some embodiments, the TOMM, TIMM, or APOE isoform polynucleotide is an Alu element-induced isoform, such as a TOMM40 isoform comprising the target region set forth in SEQ ID NO:119. In some embodiments, the antisense oligonucleotide is selected from SEQ ID NOs:1-11. The antisense oligonucleotide can comprise one or a combination of chemical modifications comprising phosphate backbone modifications, phosphorothioate (PS) backbone modification, ribose sugar group modifications, 2'-O-methyl (2OMe) modification, 2'-O-methoxy-ethyl (MOE) modification, locked nucleic acid (LNA) modification, tricyclo-DNA (tc-DNA) modification, 2'-fluoro modification, S-constrained-ethyl (cEt) modification, peptide nucleic acid (PNA) modification, or phosphorodiamidate morpholino oligomer (PMO) modification. The composition can further comprise a pharmaceutically acceptable carrier.

In some embodiments, the presently disclosed subject matter is directed to a method of reducing or eliminating the risk of neurodegenerative disease in a subject. Particularly, the method comprises modifying the Alu elements, regions immediately flanking the Alu elements, or both within one or more genes of the TOMM complex, the TIMM complex, or APOE. In some embodiments, the modifying comprises contacting the cells with one or more epigenetic regulator, such as DNA epigenetic activators, DNA epigenetic repressors, histone epigenetic activators, histone epigenetic repressors, or combinations thereof. In some embodiments, the modifying comprises targeted DNA mutation, targeted DNA excision, or combinations thereof. In some embodiments, the subject is a human.

In some embodiments, the presently disclosed subject matter is directed to a method of modulating the function, expression, or both of a TOMM, TIMM, or APOE isoform polynucleotide in the cells of a subject. The method comprises contacting the cells with an antisense oligonucleotide, wherein the oligonucleotide has at least 50%, 75%, or 95% sequence identity to a reverse complement of the TOMM, TIMM, or APOE isoform polynucleotide, thereby modulating function, expression, or both of the isoform. In some embodiments, the modulating occurs in vivo or in vitro. In some embodiments, the antisense oligonucleotide is selected from SEQ ID NO:1-11. In some embodiments, the antisense oligonucleotide is comprised within a vector system comprising one or more vectors. In some embodiments, the isoform is an Alu element-induced isoform, such as an Alu element-induced TOMM40 isoform. In some embodiments, the TOMM40 isoform comprises the target region set forth in SEQ ID NO:119. In some embodiments, the subject is a human.

In some embodiments, the presently disclosed subject matter is directed to a method of measuring the risk of a neurodegenerative disease or a disorder in a subject. The method comprises determining the methylation status of one or more genes of the TOMM complex, TIMM complex, APOE gene, or associated Alu retrotransposons and comparing the methylation status with a control, thereby identifying the risk of neurodegenerative disease or disorder. In some embodiments, determining the methylation status comprises a methylation-specific PCR analysis or methylation-specific digestion analysis. In some embodiments, the comparing comprises comparing the methylation status with the status of a confirmed neurodegenerative disease or disorder, or a negative state. In some embodiments, the subject is a human.

In some embodiments, the presently disclosed subject matter is directed to a method of measuring the risk of neurodegenerative disease or disorder in a subject, the method comprising determining the level of A-to-I RNA editing and circular RNA production of one or more genes of the TOMM complex, TIMM complex, APOE gene, or associated Alu retrotransposons and comparing the A-to-I RNA and circular RNA status with a control, thereby identifying the risk of neurodegenerative disease or disorder. Determining the A-to-I editing and circular RNA status can compriss targeted RNA sequencing. The comparing can comprise comparing the A-to-I editing and circular RNA status with the status of a confirmed neurodegenerative disease or disorder, or a negative state. In some embodiments, the subject is a human.

In some embodiments, the presently disclosed subject matter is directed to a method for treating or inhibiting a neurodegenerative condition caused by one or more TOMM, TIMM, or APOE isoform polynucleotides in the cells of a subject. The method comprises introducing a CRISPR-Cas9 genome editing system into the cells, wherein a Cas9 endonuclease is directed to one or more Alu elements or the regions immediately flanking the one or more Alu elements within the TOMM, TIMM, or APOE isoform polynucleotide in the cells of the subject by a guide RNA to produce an Alu element knockout, an Alu element mutation, or an Alu epigenetic modification. In some embodiments, the guide sequence is selected from SEQ ID NOs: 12-118. In some embodiments, the subject is a human.

BRIEF DESCRIPTION OF THE DRAWINGS

The previous summary and the following detailed descriptions are to be read in view of the drawings, which illustrate some (but not all) embodiments of the presently disclosed subject matter.

FIG. 3A is a diagram showing the amino acid sequence of normal functional TOMM40 mRNA. Ribbons indicate the formation of alpha-helices and arrows indicate the formation of beta-strands. FIG. 3A discloses SEQ ID NO: 120.

FIG. 3B is a diagram showing the amino acid sequence of Alu-induced alternative truncated isoform of TOMM40 mRNA resulting in conformational change of the TOMM40 protein. Ribbons indicate the formation of alpha-helices and arrows indicate the formation of beta-strands. FIG. 3B discloses SEQ ID NO: 121.

FIG. 8A is a diagram depicting normal function and normal pre-protein transport through the TOMM and TIMM complexes in the outer and inner mitochondrial membrane, respectively.

FIG. 8B is a diagram illustrating how Alu mediated disruption of TOMM and/or TIMM complexes can alter pre-protein transport through the outer and/or inner mitochondrial membrane. Alu-mediated disruption of the TOMM and/or TIMM complexes includes deleterious Alu mechanisms that are activated by age or stress-related modification (e.g., traumatic stress) of DNA or histone epigenetic control mechanisms (e.g., altering H3K9 histone methylation). Fluctuating epigenetic landscapes provide tissue-specific and patient-specific deleterious Alu activity.

FIG. 8C is a diagram of the brain illustrating how deleterious Alu activity cascade into a spectrum of neurodegenerative diseases (e.g., Alzheimer's, ALS, CTE, and Parkinson's disease).

DETAILED DESCRIPTION

Figure 1:
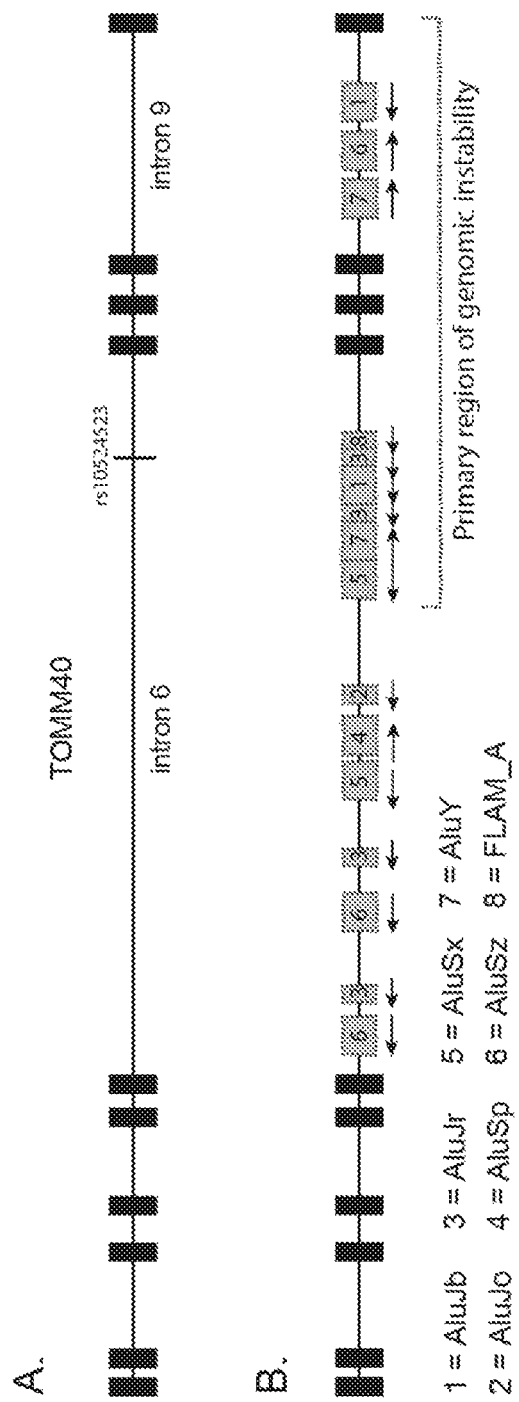
FIG. 1A is a diagram of human TOMM40 gene (Chromosome 19, GRCh38/h38 assembly; nucleotides 44,891, 220-44,903,689) with exons shown as black rectangles.
FIG. 1B is a diagram of the human TOMM40 gene of FIG. 1a illustrating the Alu elements within introns 6 and 9. A region of enhanced genomic instability arising from Alu element insertion events is identified.

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a protein" can include a plurality of proteins, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/–20%, in some embodiments +/–10%, in some embodiments +/–5%, in some embodiments +/–1%, in some embodiments +/–0.5%, and in some embodiments +/–0.1%, from the specified amount, as such variations are appropriate in the disclosed compositions and methods. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "mRNA" means the presently known mRNA and pre-mRNA transcript(s) of a targeted gene (e.g., TOMM, TIMM, or APOE isoform polynucleotide), and any further transcripts which may be elucidated.

By "antisense oligonucleotide" is meant an RNA or DNA molecule that binds to another RNA or DNA (e.g., a TOMM, TIMM, or APOE isoform polynucleotide that is mRNA, pre-mRNA, or DNA). For example, if it is an RNA oligonucleotide it binds to another RNA target by means of RNA-RNA interactions and alters the activity of the target RNA. An antisense oligonucleotide can upregulate or downregulate expression and/or function of a particular polynucleotide. The definition is meant to include any foreign RNA or DNA molecule which is useful from a therapeutic, diagnostic, or other aspect. Such molecules include, for example, antisense RNA or DNA molecules, interference RNA (RNAi), micro RNA, decoy RNA molecules, siRNA, enzymatic RNA, therapeutic editing RNA, and other oligomeric compounds that hybridize to at least a portion of the target isoform polynucleotide. As such, these compounds may be introduced in the form of single-stranded, double-stranded, partially single-stranded, or circular oligomeric compounds. The definition is further intended to include linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. More specifically, the antisense oligonucleotides of the present invention can include, but are not limited to, one or a combination of chemical modifications comprising phosphate backbone modifications, phosphorothioate (PS) backbone modification, ribose sugar group modifications, 2'-O-methyl (2OMe) modification, 2'-O-methoxy-ethyl (MOE) modification, locked nucleic acid (LNA) modification, tri-cyclo-DNA (tc-DNA) modification, 2'-fluoro modification, S-constrained-ethyl (cEt) modification, peptide nucleic acid (PNA) modification, or phosphorodiamidate morpholino oligomer (PMO) modification.

The antisense oligonucleotides having a sequence (i) capable of forming a stable complex with a portion of the targeted gene, or (ii) capable of forming a stable duplex with a portion of a mRNA or pre-mRNA transcript of the targeted gene. Stability of the complexes and duplexes can be determined by theoretical calculations and/or in vitro assays.

The term "reverse complement" is herein used interchangeably with the term "complement" for the purposes of the specification and claims.

As used herein, the term "TOMM, TIMM, or APOE isoform polynucleotide" encompasses DNA, RNA (comprising pre-mRNA and mRNA) transcribed from such DNA, and also cDNA derived from such RNA, coding, noncoding sequences, sense or antisense oligonucleotides. The specific hybridization of an antisense oligonucleotide with its TOMM, TIMM, or APOE isoform polynucleotide interferes with the normal function of the TOMM, TIMM, or APOE isoform polynucleotide. The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with TOMM, TIMM, or APOE isoform polynucleotide function is modulation of the expression of the encoded product or oligonucleotides.

RNA interference "RNAi" is mediated by double stranded RNA (dsRNA) molecules that have sequence-specific homology to their "target" nucleic acid sequences. In certain embodiments of the present invention, the mediators are 5-25 nucleotide "small interfering" RNA duplexes (siRNAs). Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

Selection of appropriate antisense oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products.

Translocases are a family of proteins that assist in moving molecules, usually across a membrane. In humans, mitochondrial translocases encode channels (e.g., β-barrel proteins) that are essential for importing proteins into the mitochondria. Mitochondria are present as organelles in eukaryotic cells and produce most of the cell's supply of ATP and are involved in several other processes (i.e., signaling, cellular differentiation, cell death, control of cell division, and cell growth). The stability of mitochondrial translocases is therefore imperative for maintaining functional mitochondria populations within cells.

Neurons are especially dependent upon healthy mitochondria populations because they do not undergo active cell division, are highly metabolically active, and require seamless mitochondrial trafficking for survival. Neuronal mitochondrial populations undergo continuous turnover and are renewed though a dynamic process of fusion, fission, and biogenesis. Disruption of the renewal process can result in abnormal function and neuron death. Particularly, mitochondrial dysfunction is believed to be a major component of multiple neurodegenerative diseases, such as AD, ALS, Parkinson's disease, and Huntington's disease. The molecular mechanisms underlying the origin of mitochondrial dysfunction are believed to include non-mendelian factors, such as tissue-specific epigenetic variation (resulting from stress, traumatic stress, aging, lifestyle factors (e.g., sleep, diet, exercise) or other environmental pressures), retrotransposition of mobile elements resulting in altered gene expression, alternative gene splicing events, and/or the formation of chimeric or fused mRNA products involving genes critical to mitochondrial function.

The translocase of the outer mitochondrial membrane (TOMM) is a complex of proteins found on the outer mitochondrial membrane of the mitochondria that allow movement of proteins and pre-proteins into the intermembrane space of the mitochondrion. The TOMM complex includes seven subunits—TOMM5, TOMM6, TOMM7, TOMM20, TOMM22, TOMM40, and TOMM70. Of these, TOMM40 forms a β-barrel protein that is the primary channel through which mitochondrial pre-proteins pass into the mitochondria. The fully assembled TOMM complex comprises three TOMM40 β-barrel channels arranged in a triangular pattern. The TOMM40 gene is located on human chromosome 19 and encodes 10 exons and nine introns. The term "exon" as used herein refers to gene regions that are transcribed into RNA and subsequently translated into proteins. As used herein, the term "intron" refers to gene regions that are transcribed into RNA molecules but that are spliced out before the RNA is translated into a protein. Structural variants within TOMM40 introns are statistically associated with cognitive impairment, thinning of the hippocampus, and neurodegenerative disease.

Further, the translocase of the inner mitochondrial membrane (TIMM) is a complex of proteins found on the inner membrane of the mitochondria that allow movement of proteins and pre-proteins across the inner mitochondrial membrane and into the mitochondrial matrix. The primary TIMM23 complex forms an import channel that consists of three essential proteins (TIMM17, TIMM23, and TIMM50) for importing molecules into the inner mitochondrial membrane and, of these, TIMM23 is critical for channel stability. The TIMM23 gene is located on human chromosome 10 (GRCh38/hg38 human genome assembly; Chr10: nucleotides 45,972,449-46,003,734).

The efficient processing of proteins that are central to mitochondrial function depends on stable TOMM and TIMM pore formation and on the seamless trafficking of proteins between the TOMM and TIMM complexes. For this reason, mitochondria are vulnerable to molecular processes that alter TOMM and TIMM stability, especially with respect to conformational changes of the channel forming proteins TOMM40 and TIMM23. The presently disclosed subject matter focuses on disrupting those processes involving retrotransposons and/or mRNA fusion events that serve to degrade mitochondrial function in neurons and contribute to the development of sporadic neurological and neurodegenerative disorders.

Retrotransposons are mobile elements that can replicate by reverse transcription of an RNA intermediate and insert themselves into new locations across the genome. There are three classes of retrotransposons: long terminal repeats (LTRs), long interspersed elements (LINEs), and short interspersed elements (SINEs). Of these, Alu elements are a highly successful primate-specific SINE and are the most abundant mobile element in the human genome, having over a million copies that comprise approximately 11% of genomic DNA. Initially considered "junk DNA", Alu elements are known to have profound impacts on gene splicing, gene expression, and gene stability. In addition, Alu elements have been implicated in a growing number of human diseases, including neurological disorders.

Alu elements include a high percentage of CpG islands (i.e., short stretches of DNA where a cytosine nucleotide is followed by a guanine nucleotide in the linear sequence of bases in a 5' to 3' direction) and are typically heavily methylated (both DNA and histone H3K9 methylation) to prevent their expression. Alu elements are approximately 300 nucleotides in length and are characterized by left and right monomers with a poly-A tail at their 3' end. Multiple subfamilies of Alu elements have been identified within humans (i.e., AluJ, AluS, AluY) and variable rates of retrotransposition have been observed across the subfamilies. Mobilization of Alu elements is mediated by the machinery of L1 retrotransposons (a subgroup of the LINE retrotransposon family) and the length of the poly-A tail facilitates retrotransposition, with Alu transposition frequency increasing with poly-A tail length. Alu elements residing within genes are transcribed by RNA polymerase II and are a part of pre-mRNA transcripts. Alu elements within pre-mRNA molecules are subject to enhanced epigenetic RNA editing (e.g., adenosine-to-inosine (A-to-I) editing) by adenosine deaminase acting on RNA (ADAR) proteins. Further, Alu elements form complex secondary structures within pre-mRNA molecules, including the formation of circular RNAs (circRNAs). Accordingly, Alu element-rich regions are susceptible to Alu element-mediated genome instability, alternative splicing events that alter protein structure/function, inhibitory pre-mRNA structures, retention and degradation of heavily A-to-I edited pre-mRNAs, and production of chimeric protein products that interfere with key cellular processes.

Figure 2A:
FIGS. 2A and 2B are diagrams representing double stranded RNA structure within TOMM40 intron 6 and intron 9, respectively, resulting from Alu elements arranged in opposite orientation.
Figure 2B:
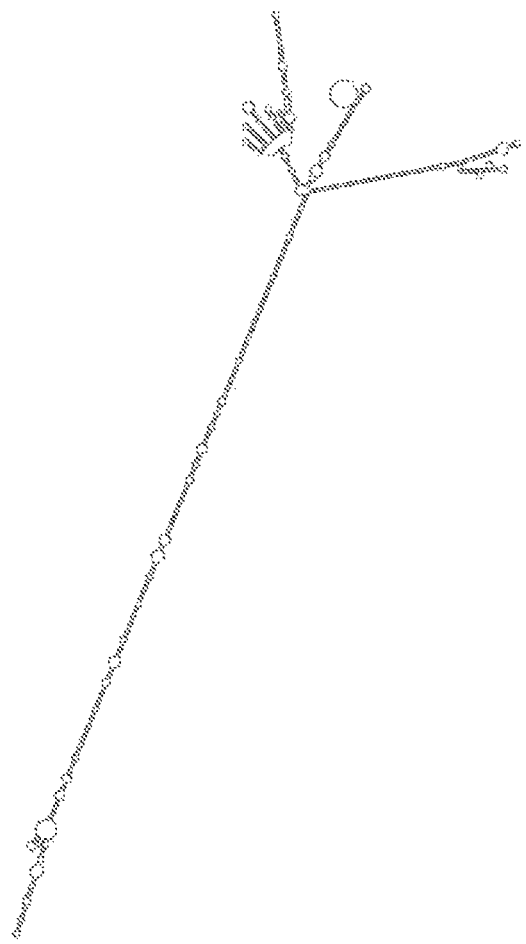

FIG. 1A is a diagram of the human TOMM40 gene (GRCh38/hg38 assembly; Chr19 nucleotides 44,891,220-44,903,689) with exons shown as grey rectangles. Primate-specific Alu retrotransposons have repeatedly inserted into TOMM40 introns. FIG. 1A also shows a variable deoxythymidine homopolymer repeat (poly-T; variant rs10524523, statistically associated with cognitive impairment, hippocampal thinning, and late-onset Alzheimer's disease risk) that is part of an Alu element and originated from an Alu insertion event. As shown in FIG. 1B, sixteen Alu elements have inserted themselves across TOMM40 introns 6 and 9. The dashed line below the gene diagram identifies the primary region of enhanced genomic instability of the TOMM40 gene associated with Alu elements. Age, stress, lifestyle factors (e.g, sleep, diet, exercise), and other environment related epigenetic modification (e.g., both hyper- and hypomethylation), de novo Alu element insertion events, excessive Alu A-to-I RNA editing, introduction of premature stop codons, and/or exonization of Alu elements within the region is believed to contribute to either alternative mRNA splicing events of TOMM40 or increased degradation of TOMM40 mRNAs. The arrows in FIG. 1B show Alu element orientation of insertion events across TOMM40. Alu elements having opposite orientation contribute to double stranded RNA structures impacting TOMM40 gene expression. FIGS. 2A and 2B illustrate one embodiment of the double stranded RNA structure within TOMM40 intron 6 and TOMM40 intron 9, respectively, resulting from Alu elements arranged in opposite orientations.

The Alu transposons in TOMM40 introns 6 and 9 contribute to transcriptional noise through elevated non-sense mediated decay (e.g., due to enhanced A-to-I editing) and/or the production of alternative TOMM40 isoforms. Genetic variants of TOMM40 have been associated with dementia and neurodegenerative disease. Specifically, both single nucleotide polymorphisms (SNPs) and short structural variants (SSV) within TOMM40 have been implicated in a number of neurological disorders, ranging from mild cognitive impairment to major neurodegenerative diseases (such as LOAD and PD). Disrupting the TOMM complex effectively triggers a mitochondrial stress response and can ultimately lead to inflammation and mitophagy, a process that exhibits devastating consequences across neurological networks.

Further, tissue-specific aging, stress, lifestyle factors (e.g., sleep, diet, exercise) and/or environmentally-associated epigenetic modification of Alu elements (i.e., both DNA and histone H3K9 methylation or acetylation) within TOMM40 introns 6 and/or 9 is believed to contribute to an increase of alternative splicing events of TOMM40 and/or to increased production of modified TOMM40 proteins thereby contributing to the establishment of dysfunctional TOMM pores (resulting in protein aggregate accumulation) and/or decreased mitochondrial populations in neurons. In addition, the Alu element-rich 3' region of TOMM40 is unstable due to multiple Alu element insertion events that can contribute to the formation of double-stranded pre-mRNA structures (including circRNAs) and enhanced A-to-I editing of pre-mRNA molecules that effectively alters TOMM40 gene expression leading to mitochondrial stress and dysfunction.

The relative age of each Alu element and the orientation of Alu element insertion events play an essential role with respect to potential Alu element exonization and downstream recombination events that can serve to disrupt TOMM40 mRNA transcripts. Alu element-associated poly-T regions resulting from antisense insertion events (FIG. 1A) are known to destabilize gene transcription and contribute to increasing levels of mRNA degradation. Collectively, these observations identify a region of enhanced genomic instability in TOMM40 that is vulnerable to several Alu element-associated pathways proven to alter gene expression and is implicated in a growing list of human diseases.

Figure 3B:
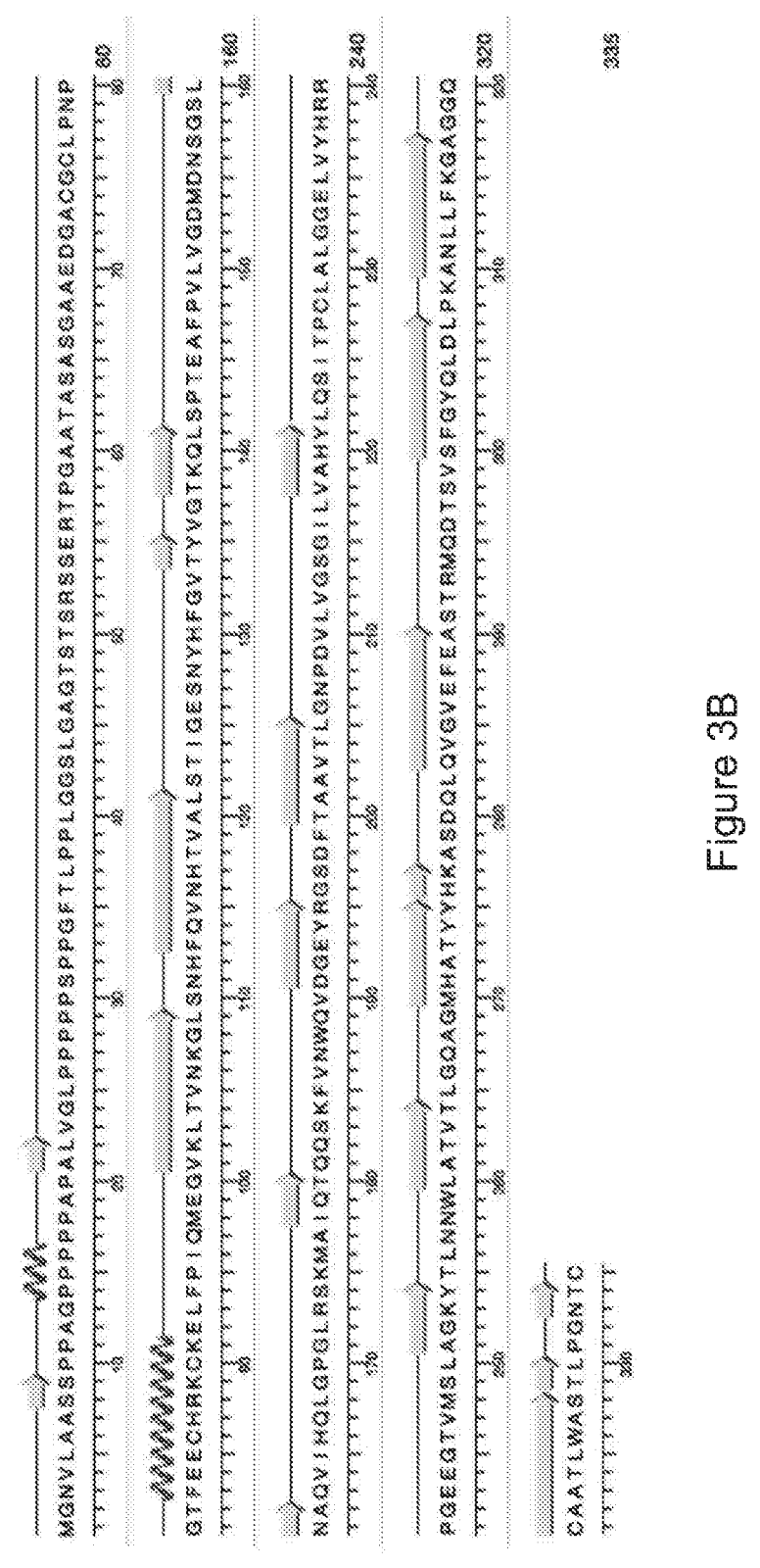

Inverted-repeat Alu elements, such as those distributed across TOMM40 introns 6 and 9, can disrupt mRNA stability by facilitating premature transcription termination and altering A-to-I RNA editing. The Alu elements enriched across the 3' end of TOMM40 are believed to contribute to the production of modified yet functional transcripts that escape nonsense-mediated mRNA decay and directly alter the TOMM40 protein conformation. For example, three Alu elements within TOMM40 intron 9 are associated with an alternative splicing event that results in a mRNA product of 335 amino acids in length, 26 amino acids shorter than the normal TOMM40 mRNA product. FIG. 3A is a diagram showing the amino acid sequence of normal functional TOMM40 mRNA (NCBI GenBank accession number CP_006105; 361 amino acids in length; protein strands and helices are shown in arrows and spirals). FIG. 3B is a diagram showing the amino acid sequence of Alu-induced alternative truncated isoform of TOMM40 mRNA (NCBI GenBank accession XM_005258468; 335 amino acids in length).

Figure 4:
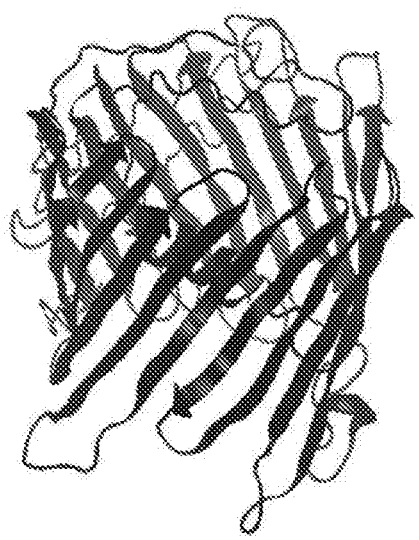
FIG. 4A is a protein model of normal TOMM40 protein (i.e., Tom40) structure.
FIG. 4B is a protein model of truncated TOMM40 gene with alternative gene transcripts arising from dysregulation of Alu elements that influence Tom40 protein conformation.
Figure 4:

Predictive modeling suggests that a β-barrel protein conformation may still form from the truncated TOMM40 isoform. However, the modified form would likely display functional differences from normal TOMM40, serving to restrict the passage of pre-proteins and/or destabilizing the TOMM complex. To this end, protein products implicated in neurodegenerative disease (e.g., amyloid precursor protein) are known to lodge within, block, and accumulate at the TOMM complex. FIG. 4A is a 3-dimensional model of the normal TOMM40 protein structure. FIG. 4B is a predictive 3-dimensional model showing the potential influence of premature termination of the TOMM40 gene transcript on the TOMM40 protein structure. The 3' end of the truncated 335 amino acid transcript coincides with the AluY retrotransposon within intron 9 of TOMM40 (as shown in FIG. 1). The regions marked with reference numerals 1, 2, and 3 identify major conformational changes to the β-barrel protein. Without being restricted to any particular mechanism of action, it is proposed that conformational changes of TOMM40 may contribute to the initial formation of inflammatory protein bodies observed in neurodegenerative disease.

Figure 5:
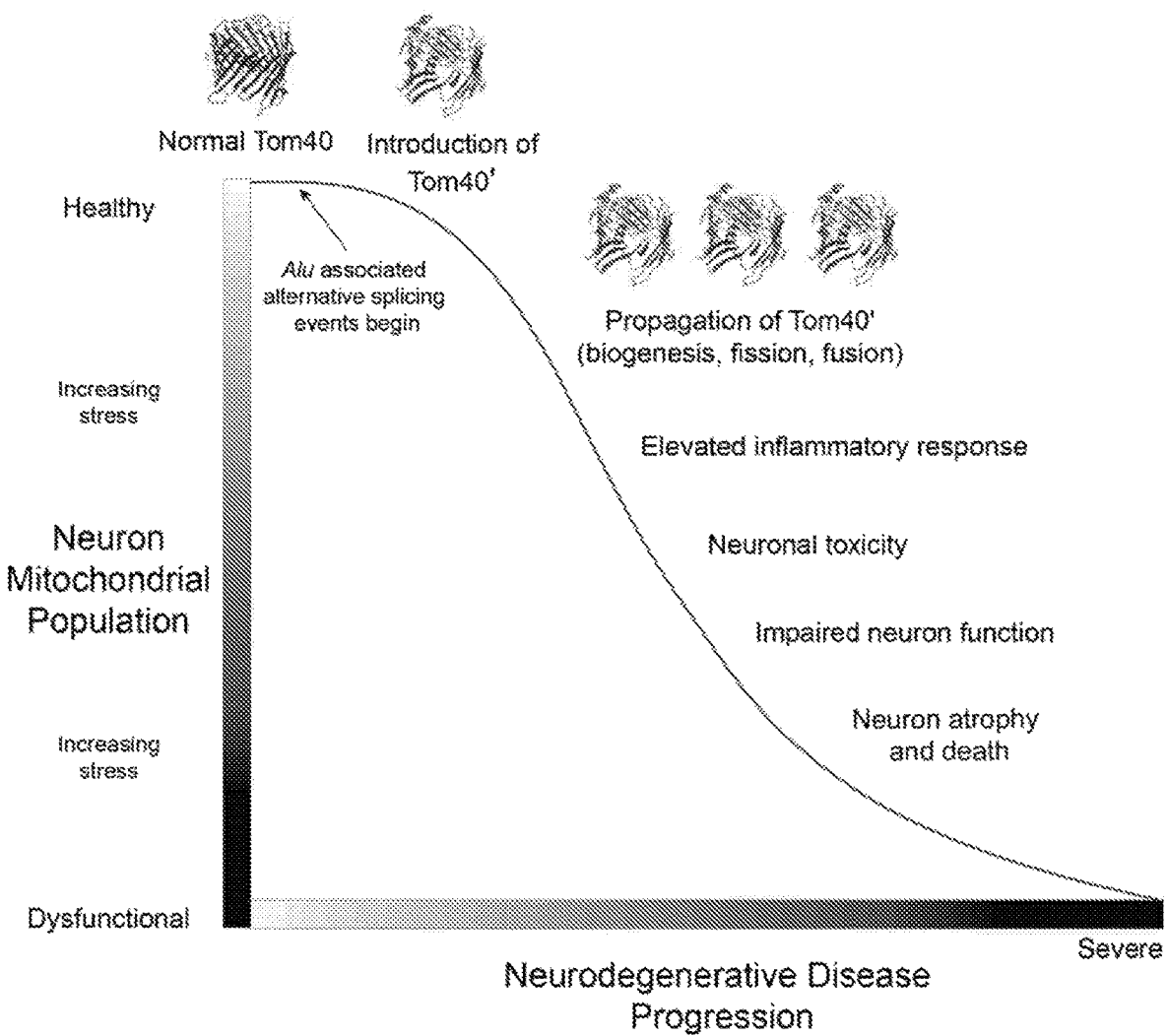
FIG. 5 is a model illustrating alternative isoforms of TOMM40 (i.e., Tom40 proteins) cascading into neurodegenerative disease.

Alu element-associated disruption of normal mRNA processing of TOMM40 may result in increased localization of the paralog TOMM40L to the mitochondrial outer membrane. As a result, the efficient processing of mitochondrial pre-proteins can be modified and/or the TOMM complex can be otherwise destabilized. Such a mechanism could result in the propagation of inefficient TOMM channels through mitochondrial biogenesis, fusion, and fission within individual neurons over variable time-scales, as shown in FIG. 5. This mechanism can account for the initial establishment and accumulation of intra-cellular protein bodies that are the hallmark of multiple neurodegenerative disorders.

Figure 6:
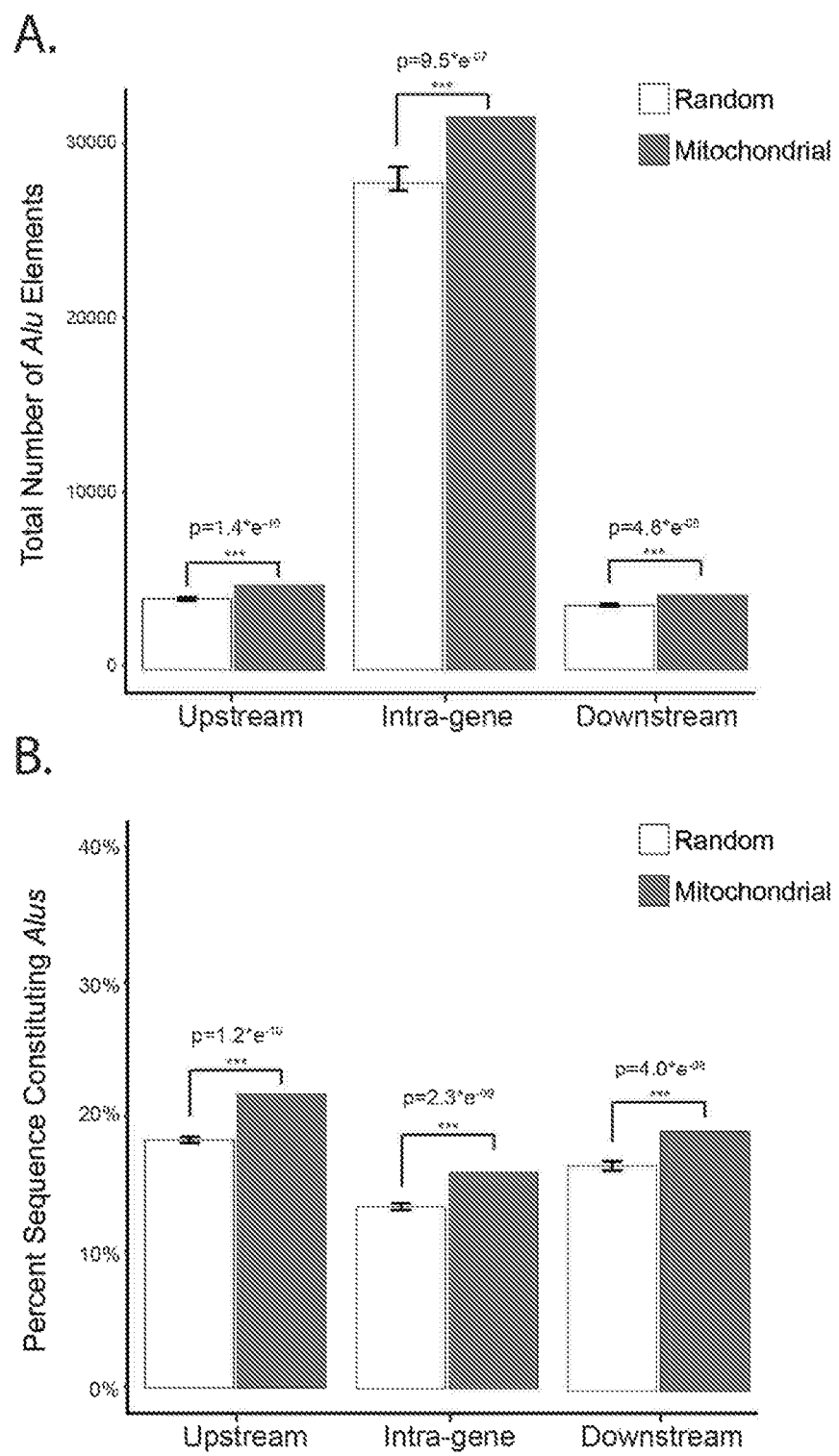
FIGS. 6A and 6B are graphs showing elevated Alu insertion events across nuclear-encoded mitochondrial genes within the human genome.

Alu element exonization and somatic retrotransposition events of both L1 and Alu elements have been identified in multiple TOMM genes (i.e., TOMM5, TOMM7, TOMM22, TOMM40, TOMM40L), indicating that TOMM genes are actively influenced by and are vulnerable to retrotransposons, likely owing to their high transcription rates and open chromatin status. In light of these observations, the transcriptionally active 2,000 nuclear-encoded genes that are essential for mitochondrial function are especially vulnerable to retrotransposon disruption, particularly within energetically demanding neurons. Given this hypothesis, it would be expected that nuclear-encoded mitochondrial genes would display an enrichment of mobile elements with respect to other genes. An analysis of the mobile element content of 1,145 genes that encode mitochondrial proteins as well as an additional 8,973 randomly selected protein-coding genes throughout the human genome provides statistical support for an enrichment of Alu mobile elements within and adjacent to mitochondrial genes, as illustrated in FIG. 6. Thus, transcriptionally active nuclear-encoded genes that are essential for mitochondrial function are vulnerable to deleterious retrotransposon-related mechanisms known to disrupt gene expression pathways. If operating within energetically demanding neurons, retrotransposon-related destabilization of efficient transcription and translation of mitochondrial genes would contribute to the activation of inflammatory response pathways that can cascade to neuronal tissue damage and neurodegenerative disease.

The human genome has evolved a number of mechanisms to defend against deleterious retrotransposon activity, including DNA methylation, histone methylation, and RNA degradation using miRNA-processing enzymes. With respect to Alu elements, epigenetic silencing is predominantly mediated by histone (H3K9) methylation to suppress transcription and retrotransposition. Hypomethylation (loss of the methyl group in the 5-methylcytosine nucleotide) contributes to enhanced retrotransposon activity, which in turn can increase transcriptional noise by disrupting gene expression pathways, inducing alternative splicing events and reducing mRNA stability. Genome-wide Alu element hypomethylation is part of the aging process, and global hypomethylation of Alu elements has been statistically associated with Alzheimer's disease, multiple sclerosis, osteoporosis, and many forms of cancer. Moreover, both DNA and histone methylation landscapes can be altered by both lifestyle factors (e.g., sleep, diet, exercise) and traumatic stress events (e.g., brain injury arising from concussion). Thus, there is believed to be a link between age and environment-associated epigenetic modifications of Alu elements and a range of sporadic neurological disorders and human diseases. Particularly, elevated retrotransposon activity in the human central nervous system, mediated by epigenetic regulation for beneficial neurological function and to reduce deleterious events, is accompanied by enhanced vulnerability in neurons resulting in neurological disease.

Figure 7:
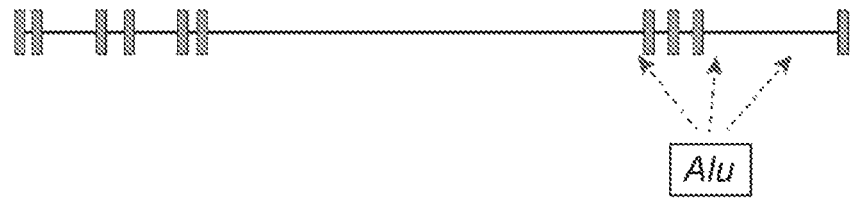
FIG. 7A is a diagram representing de novo Alu retrotransposition events.
FIG. 7B is a diagram representing the formation of secondary structures (inverted-repeat Alu duplexes) within pre-mRNA transcripts.
FIG. 7C is a diagram representing hypomethylation of Alu contributing to exonization. The figure represents both DNA and histone hypomethylation.
Figure 7:
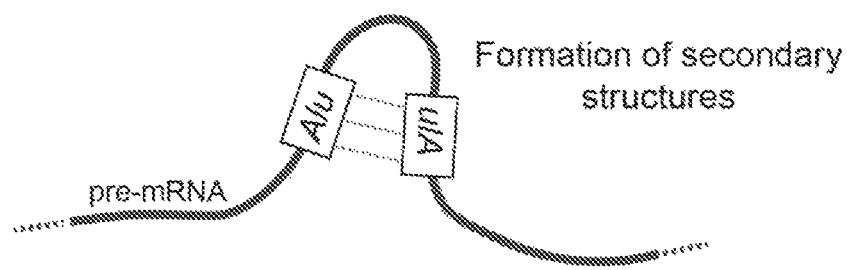
Figure 7:
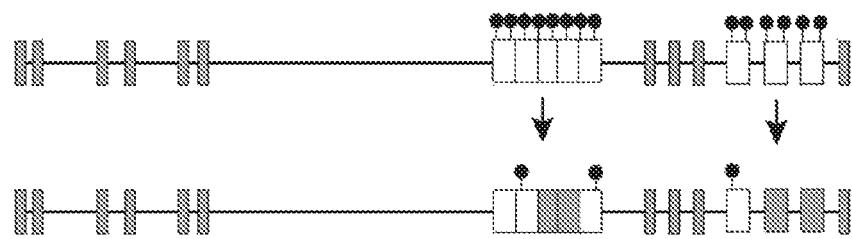

Epigenetic modification (including both hyper- and hypomethylation) of Alu elements and/or de novo Alu element insertions within (or in close proximity to) genes that are essential to mitochondrial function (such as TOMM40) are believed to contribute to mRNA instability, ultimately leading to mitochondrial dysfunction. For example, retrotransposons can influence gene splicing by de novo Alu element retrotransposon events (as illustrated in FIG. 7A), through the formation of inverted repeat Alu element duplexes within pre-mRNA transcripts (as illustrated in FIG. 7B), and through hypomethylation of Alu elements that contribute to exonization (as illustrated in FIG. 7C).

Furthermore, histone H3K9 also regulates APOE transcription. APOE (apolipoprotein E) is essential for the normal catabolism of triglyceride-rich lipoprotein constituents. Variants of the APOE gene are statistically associated with Alzheimer's disease onset. The Alu element-rich regions of TOMM40 are immediately upstream of APOE on human chromosome 19. The epigenetic interaction between Alu elements within TOMM40 and the APOE promoter (resulting from antagonistic hypo- or hyper-methylation of H3K9) is believed to influence TOMM40 gene expression and/or APOE gene expression. Thus, there is believed to be an epigenetic link between time-dependent mitochondrial dysfunction (both slowly accumulating or accelerated) and tissue-specific idiopathic neurodegenerative disease.

Figure 8:
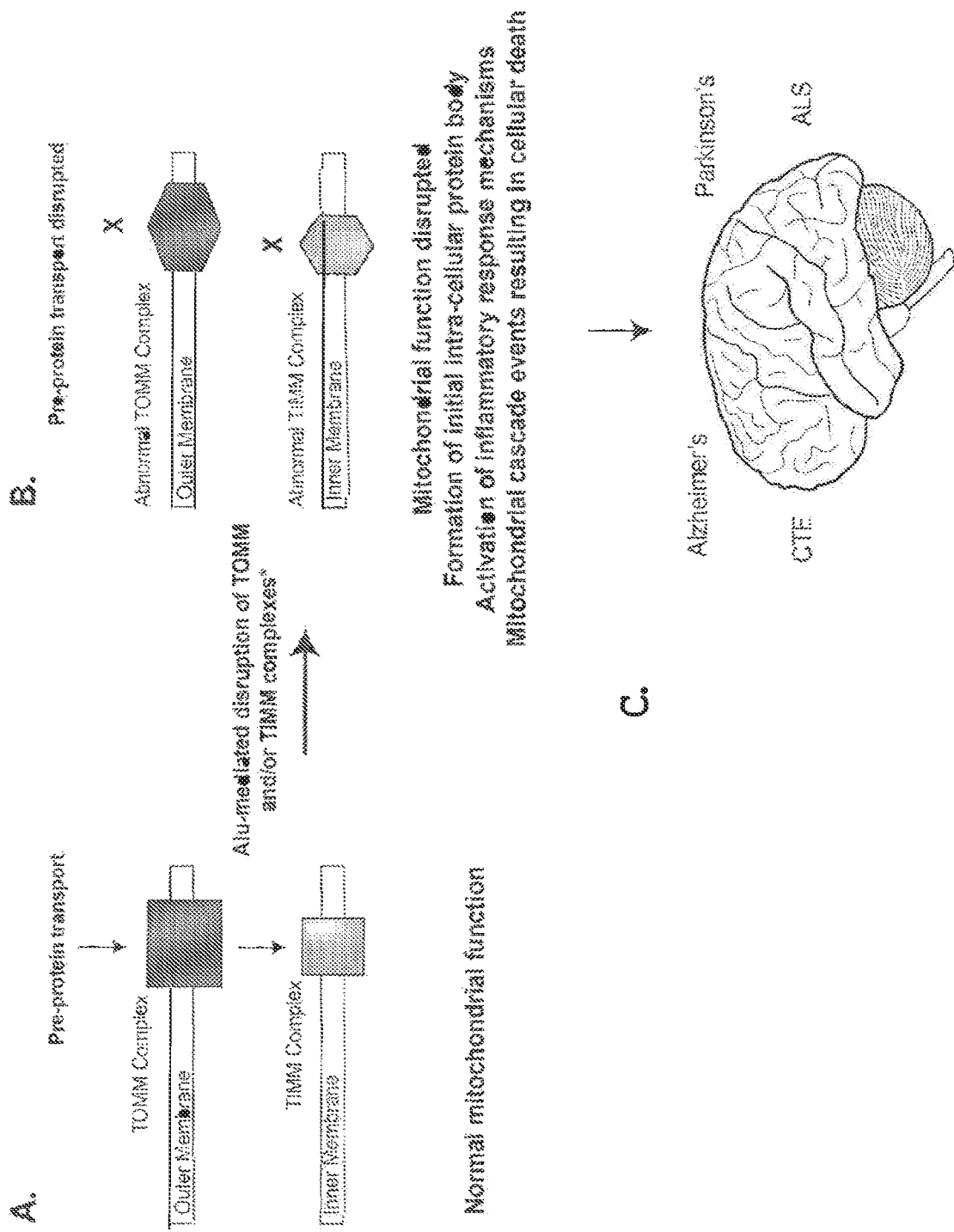
FIG. 8 is a model illustrating how Alu mediated disruption of TOMM and/or TIMM complexes, embedded within the outer and inner mitochondrial membrane, can result in neurodegenerative disease.
Figure 9:
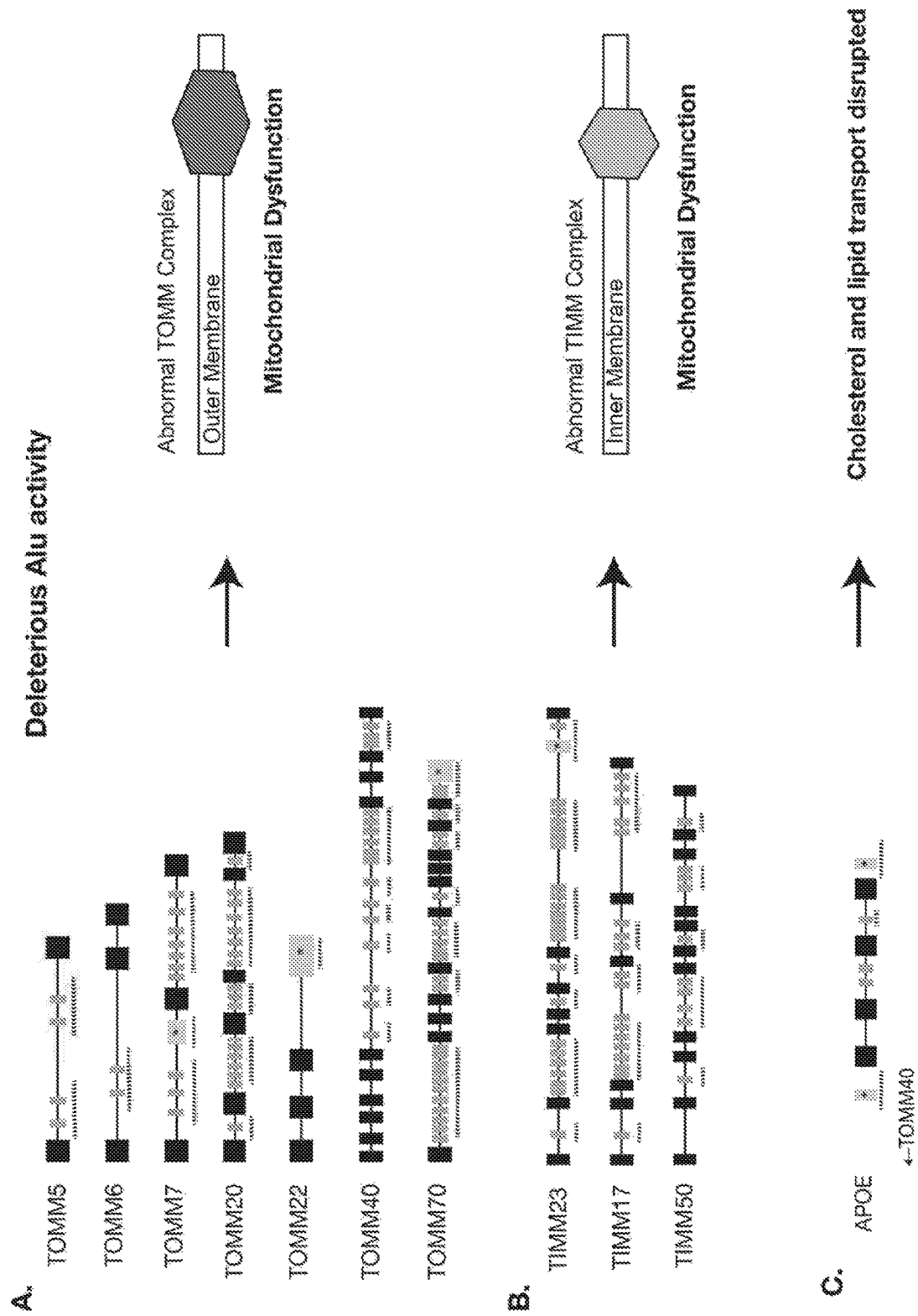
FIG. 9A is a diagram representing genes of the TOMM complex that are subject to deleterious Alu activity. Black boxes identify exons within each gene and gray boxes identify Alu elements that introduce genomic instability. Therapeutic target regions are identified by dashed lines. Asterisks identify Alu elements within exons that directly alter protein function. Collectively, the deleterious Alu activity of TOMM genes contributes to mitochondrial dysfunction by destabilizing the translocase of outer mitochondrial membrane (TOMM) complex.
FIG. 9B is a diagram representing genes of the TIMM complex that are subject to deleterious Alu activity. Black boxes identify exons within each gene and gray boxes identify Alu elements that introduce genomic instability. Therapeutic target regions are identified by dashed lines. Asterisks identify Alu elements within exons that directly alter protein function. Collectively, the deleterious Alu activity of TIMM genes contributes to mitochondrial dysfunction by destabilizing the translocase of inner mitochondrial membrane (TIMM) complex.
FIG. 9C is a diagram representing the APOE gene that is subject to deleterious Alu activity. Black boxes identify exons within each gene and gray boxes identify Alu elements that introduce genomic instability. Therapeutic target regions are identified by dashed lines. Asterisks identify Alu elements within flanking regions that can influence the epigenetic regulation of APOE. The TOMM40 gene is immediately adjacent to APOE and the Alu epigenetic landscape of TOMM40 can influence the APOE promoter. Collectively, the deleterious Alu activity within and surrounding APOE contributes to altered cholesterol and lipid processing.

Recent data from single-cell genome sequencing provides evidence of unique or mosaic genomes of individual neurons arising from enhanced retrotransposon activity both during neurogenesis and throughout life. Thus, individual neurons can have differing intracellular conditions that influence gene transcription, translation, and protein formation. Mitochondrial genes encoded within the nuclear genome are particularly vulnerable to enhanced retrotransposon activity (including elevated Alu-based epigenetic RNA editing and production of Alu-based circular RNAs) given their high expression and open chromatin status within neurons. This vulnerability increases with age, stress, lifestyle factors (e.g., sleep, diet, exercise), and/or environmental conditions that alter the epigenetic landscape of neurological networks (as described above). Therefore, retrotransposons, operating though human-specific neurological pathways, are believed to contribute to environment, stress, lifestyle, and/or age-related neurodegeneration by disrupting functional mitochondrial populations within neurons (FIG. 8). The mitochondrial disruption can occur through a number of retrotransposon-induced mechanisms that can influence the efficient and accurate transcription and/or translation of the ~2,000 mitochondrial genes encoded in the nuclear genome (FIGS. 6A and 6B). In light of TOMM40, it is believed that Alu element-related conformational changes (both subtle and major) of the outer and inner mitochondrial membrane pores restrict or prevent the normal translocation of proteins (i.e., TOMM and TIMM complexes), ultimately contributing to mitochondrial stress and mitophagy. The vulnerability can be amplified through mitochondrial biogenesis and downstream mitochondrial fission and fusion events, thus contributing to the initial establishment of inefficient mitochondria that increase mitochondrial stress over time, contribute to the formation of protein aggregates, and limit neuron functionality, ultimately cascading into a diseased state (FIG. 8).

Under this framework, retrotransposon-mediated dysfunctional mitochondrial cascade events can manifest in different neurological tissues. The initiation of tissue-specific cascade events, operating through variable inter-cellular and intra-cellular conditions and occurring at different life stages, can ultimately result in diseased states that share similar underlying pathologies with patients displaying a spectrum of neurological impairments. Moreover, tissue-specific deleterious cascade events can originate from traumatic stress events known to disrupt retrotransposon epigenetic control mechanisms (including physical and emotional trauma).

In some embodiments, Alu-induced protein isoforms can be reduced using antisense therapy (i.e., mRNA antisense oligonucleotides). An "antisense" oligonucleotide comprises a nucleotide sequence that is complementary to a "sense" nucleic acid, e.g., complementary to the mRNA sequence of a target. Once the antisense oligonucleotide binds to the target mRNA, the associated gene is inactivated (i.e., turned off) because mRNA must be single stranded for translation to occur. In some embodiments, the target mRNA can be can be an Alu element-induced isoform of TOMM and TIMM gene products, or the APOE gene. For example, in some embodiments, the isoform can be an Alu element-induced TOMM40 isoform. The term "isoform" as used herein refers to an analog or mutant having one or more amino acid modifications at one or more amino acid positions of a natural fully-functional human protein. In some embodiments, the antisense oligonucleotides can span both normal sequences and Alu element sequences within TOMM, TIMM, or APOE isoform mRNA.

The disclosed antisense oligonucleotides can be administered to a subject or generated in situ such that they hybridize with or bind to cellular mRNA encoding the isoform to thereby inhibit translation. The hybridization can be through conventional nucleotide complementarity to form a stable duplex.

In some embodiments, the antisense nucleic acid molecule can be administered systemically and modified to target selected cells. For example, for systemic administration, an antisense molecule can be modified such that it specifically binds to a TOMM, TIMM, or APOE isoform on a selected cell surface, e.g., by linking the antisense nucleic acid molecule to a peptide or an antibody that binds to a cell surface receptor or antigen. The antisense nucleic acid molecule can also be delivered to cells using a vector system, as would be known to those of ordinary skill in the art.

Thus, in some embodiments, the presently disclosed subject matter is directed to a composition comprising one or more antisense oligonucleotides specific for an isoform of TOMM, TIMM, or APOE polynucleotide.

In some embodiments, a pharmaceutically acceptable amount of the disclosed antisense oligonucleotides is administered. The term "pharmaceutically acceptable" as used herein refers to a material that is not biologically or otherwise undesirable (i.e., the material can be incorporated into a pharmaceutical composition administered to a patient without causing any undesirable biological effects or interacting in a deleterious manner with any of the other components of the composition).

Accordingly, the presently disclosed subject matter can comprise methods of modulating the function and/or expression of a TOMM, TIMM, or APOE isoform in a subject's cells or tissues. In some embodiments, the modulation can be in vivo or in vitro. In some embodiments, the method comprises contacting the cells or tissues of a subject (i.e., a human) with at least one antisense oligonucleotide, whereby the oligonucleotide has at least about 50% sequence identity (i.e., at least about 50, 55, 60, 65, 70, 75, 80, 85, 86, 87, 88, 89, 90, 91, 92, 93, 94, 95, 96, 97, 98, 99, or 99.9%) to a reverse complement of an isoform of TOMM, TIMM, or APOE, such that function and/or expression of the isoform polynucleotide is modulated in the cells/tissue.

The antisense oligonucleotides described herein can comprise any pharmaceutically acceptable salts, esters, or any other functional chemical equivalent that, upon administration to subject (e.g., a human) is capable of providing (directly or indirectly) the biologically active metabolite or residue thereof. Accordingly, the presently disclosed subject matter includes prodrugs and pharmaceutically acceptable salts of the antisense oligonucleotides disclosed herein, pharmaceutically acceptable salts of such prodrugs, and other bio equivalents. As used herein, the term "prodrug" refers a therapeutic agent that is prepared in an inactive or less active form that is converted to an active form (i.e., drug) within the body or cells thereof by the action of endogenous enzymes, chemicals, and/or conditions. As used herein, the term "pharmaceutically acceptable salts" refers to physiologically and pharmaceutically acceptable salts of the disclosed compounds (i.e., salts that retain the desired biological activity of the parent compound and do not impart undesired toxicological effects thereto). For example, sodium salts of antisense oligonucleotides are useful and are well accepted for therapeutic administration to humans. The disclosed antisense oliogonucleotides can be admixed, encapsulated, conjugated or otherwise associated with other molecules, molecule structures, or mixtures of compounds.

The antisense oligonucleotides described herein can comprise one or a combination of chemical modifications to enhance stability against degradation by endo-and exonucleases and/or to improve targeting to the cells of interest. Methods for such improvement of the pharmacological profile of antisense oligonucleotides are known to those of skill in the art (see, e.g., Evers et al. (2015) Advanced Drug Delivery Reviews 87:90-103). For example, antisense oligonucleotides can be prepared having a range of different modifications on the phosphate backbone and ribose sugar group in the case of RNA. More specifically, the antisense oligonucleotides of the present invention can include, but are not limited to, one or a combination of chemical modifications comprising phosphate backbone modifications, phosphorothioate (PS) backbone modification, ribose sugar group modifications, 2'-O-methyl (2OMe) modification, 2'-O-methoxy-ethyl (MOE) modification, locked nucleic acid (LNA) modification, tricyclo-DNA (tc-DNA) modification, 2'-fluoro modification, S-constrained-ethyl (cEt)

modification, peptide nucleic acid (PNA) modification, or phosphorodiamidate morpholino oligomer (PMO) modification.

The antisense oligonucleotides of the present invention can be administered intraventricularly, intranasally, intrathecally, or systemically to the subject.

In some embodiments, the antisense oligonucleotides are tagged with a cell-penetrating peptide (CPP) for systemic administration, such as intravenous administration, in order to allow for passing of the blood brain barrier.

In some embodiments, the antisense oligonucleotides are encapsulated in exosomes for systemic administration, such as intravenous administration, in order to allow for passing of the blood brain barrier.

In some embodiments, the presently disclosed subject matter is directed to a method of measuring, reducing, and/or eliminating the risk of mitochondrial dysfunction and/or neurodegenerative disease by modifying the Alu elements and/or regions immediately flanking Alu elements within one or more genes of the TOMM complex (including the paralog of TOMM40, TOMM40L), one or more genes of the TIMM protein complex, and/or Apolipoprotein E (APOE). For example, in some embodiments, the Alu elements and flanking regions can be modified by epigenetic regulators (e.g. DNA and/or histone epigenetic activators and/or repressors), targeted DNA mutation, and targeted excision, or combinations thereof. Moreover, in some embodiments, targeted bioassays of the methylation status of one or more genes of the TOMM complex, one or more genes of the TIMM complex, the APOE gene, and/or associated Alu retrotransposons can be performed to determine neurodegenerative disease risk or progression status.

Particularly, the Alu elements within or adjacent to genes encoding proteins of the TOMM and/or TIMM complexes and/or the APOE gene can be epigenetically modified or disrupted using a therapy comprising of clustered regularly interspaced short palindromic repeats (CRISPR)-Cas genome editing technology that can target specific DNA sequences within a given genome. CRISPR-Cas9 includes the use of a Cas9 protein and one or more guide RNAs targeting the desired sequence. In this system, the target sequence is contacted with a CRISPR-associated Cas protein and 1-2 ribonucleic acids, where the ribonucleic acids direct the Cas protein to and hybridize to the target. The target polynucleotide sequence is then cleaved by the Cas9 protein that has DNA endonuclease activity. In some embodiments, CRISPR-Cas9 mediated epigenetic repression of Alu elements is achieved by utilizing short (~14 base pairs) single-guide (or small-guide) RNA (sgRNA) sequences that bind to DNA regions immediately flanking Alus. When combined with CRISPR-Cas9 these short sgRNA will allow for Cas9 binding without cleaving the target locus. Binding of the Cas9 complex serves to repress Alu activity. In some embodiments, epigenetic repression of Alu elements is achieved using CRISPR/dCas9-KRAB and other chromatin-modifying enzymes with guide RNA sequences targeting Alu elements within or neighboring TOMM, TIMM, and/or the APOE gene.

Targeted CRISPR-Cas9 DNA mutation or excision of Alu elements within or neighboring TOMM, TIMM, and/or the APOE gene is achieved by inducing double-strand breaks that are then repaired by native non-homologous end joining or homology-directed repair pathways, to those regions immediately flanking Alu elements. CRISPR-Cas9 guide RNAs targeting those flanking regions are provided below (Table 1).

Thus, in some embodiments, the transcriptome, genome, and epigenome of an organism can be manipulated using targeted antisense oligonucleotide and/or CRISPR/Cas9 or technologies or another technology similar to CRISPR/Cas9. For example, in some embodiments, the presently disclosed subject matter includes composition that can be administered to a subject. Therapeutic delivery of antisense oligonucleotides and/or CRISPR-components that target Alu related isoforms of TOMM, TIMM, or APOE genes and/or regions flanking Alu elements (as described above) can include, but are not limited to, viral vectors including adeno-associated virus (AAV), lipid-mediated delivery including liposomes and/or related lipid nanoparticles, nanogels, electroporation, and polyethylenimine mediated transfection. In some embodiments, the presently disclosed subject matter is directed to a therapeutic genome editing method for treating or inhibiting a condition (such as a neurological condition) caused by Alu retrotransposons related to TOMM, TIMM, or APOE genes and proteins.

In some embodiments a method is provided of modulating the function, expression, or both of a TOMM, TIMM, or APOE isoform polynucleotide in the cells of a subject, the method comprising: contacting said cells with an antisense oligonucleotide, wherein said oligonucleotide has at least 50% sequence identity to a reverse complement of a TOMM, TIMM, or APOE isoform polynucleotide, thereby modulating function, expression, or both of the isoform. The modulating can occur in vivo or in vitro. The antisense oligonucleotide can be selected from SEQ ID NOs:1-11. The antisense oligonucleotide can be comprised within a vector system comprising one or more vectors. The antisense oligonucleotide can have at least 75% sequence identity to a reverse complement of a TOMM, TIMM, or APOE isoform polynucleotide. The antisense oligonucleotide can have at least 95% sequence identity to a reverse complement of a TOMM, TIMM, or APOE isoform polynucleotide. The TOMM, TIMM, or APOE isoform polynucleotide can be an Alu element-induced isoform. The TOMM, TIMM, or APOE isoform polynucleotide can be an Alu element-induced TOMM40 isoform. The TOMM40 isoform can comprise the target region set forth in SEQ ID NO:119. The subject can be a human.

In some embodiments, the methylation status of Alu elements within or neighboring TOMM and TIMM genes, and/or the APOE gene, can be stabilized or restored using histone deacetylases inhibitors (HDACis) and/or thiazolidinedione compounds (TZDs) comprised of short chain fatty acids, hydroxamic acids and benzamides including but not limited to nicotinamide, VPA, sodium butyrate, TSA, SAHA, phenylbutyrate, Ex527, and benzamide ms-275. Therapeutic delivery mechanisms of Alu stabilizing HDACis and TZDs can include, but are not limited to, oral delivery, cerebrospinal delivery via lumbar puncture, lipid-mediated delivery including liposomes and/or related lipid nanoparticles, nanogels, electroporation, polymer-based particles, and polyethylenimine mediated transfection.

In some embodiments, epigenetic processes centered on Alu elements within TOMM, TIMM, and APOE pre-mRNAs and mRNAs can be measured for biomarker/epimarker analyses using targeted high-throughput sequencing technologies (e.g., ILLUMINA TECHNOLOGIES), targeted Sanger sequencing, and/or targeted single-molecule sequencing (e.g., PACIFIC BIOSCIENCES and/or OXFORD NANOPORE TECHNOLOGIES). These processes include, but are not limited to, A-to-I editing levels and/or presence or absence of circular RNAs associated with TOMM, TIMM, and/or APOE genes. Results from premRNA biomarker analyses can be used to determine or quantify neurodegenerative disease risk with respect to epigenetic Alu-related pathways discussed herein.

In some embodiments, DNA and/or histone methylation status of Alu elements within or neighboring TOMM and TIMM genes, and/or the APOE gene (Table 3), can be measured for biomarker/epimarker analyses using targeted bisulfite-sequencing, chromatin immunoprecipitation high-throughput sequencing (ChIP-seq), single-molecule real-time sequencing (e.g. Pacific Biosciences Technologies), and/or single-molecule nanopore sequencing (e.g. Oxford Nanopore Technologies). Targeted epimarker analyses will be performed using baits or probes designed to bind to conserved regions within TOMM and TIMM genes and/or the APOE gene (coordinates provided in Table 3). In some embodiments, the biological samples required for biomarker/epimarker analyses would include peripheral blood and/or cerebrospinal fluids. The DNA and/or histone methylation status of Alu elements within and/or neighboring TOMM, TIMM, and/or the APOE gene will be used to measure and/or predict Alu-related destabilization of genes essential to mitochondrial function. In some embodiments, biomarker/epimarker analyses of Alu elements within TOMM, TIMM, and/or APOE gene will focus on individual or patient-specific Alu variation arising from maternal, paternal, and/or de novo insertion events and will include phased analyses. Results from the Alu biomarker/epimarker assay will be used to help determine or quantify neurodegenerative disease risk with respect to the Alu-related molecular pathways discussed herein.

In some embodiments, the method can be carried out in vivo or ex vivo.

The presently disclosed subject matter is not limited to neuronal mitochondrial dysfunction and neurodegenerative disease. Particularly, beyond neurodegenerative disease, mitochondrial dysfunction can underlie the origin of a wide variety of human diseases including (but not limited to) cancer (e.g., prostate, liver, brain, colon, lung, gastric, breast, leukemia, ovary, thyroid, salivary, goiter, kidney), cardiovascular disease (e.g., atherosclerosis, ischemic heart disease, heart failure, hypertension), metabolic disease (e.g., insulin resistance, diabetes, obesity-associated metabolic syndrome, dysglycemia, dyslipidemia), inflammatory disease, and osteoporosis. Therefore, the compositions and methods provided herein to interfere with the retrotransposon or Alu-mediated molecular mechanisms applicable to nuclear-encoded mitochondrial genes associated with a broad range of human diseases.

Alu-related molecular mechanisms that can disrupt the efficient transcription and/or translation of nuclear-encoded mitochondrial genes can include (but are not limited to) de novo Alu insertion, Alu exonization, altered RNA editing, altered adenosine-to-inosine (A-to-I) editing, premature gene translation termination, alternative gene splicing, non-homologous recombination events, altered micro-RNA regulation, altered binding of long non-coding RNAs, hypomethylation, and hypermethylation. If operating across select tissue types (e.g., brain, heart, liver, spleen, pancreas, lung, kidney, prostate, ovary, breast, colon), the disruptive Alu mechanisms are a plausible source for human disease wherein incipient or early mitochondrial dysfunction is hypothesized. Moreover, epigenetic control mechanisms of Alu elements dissipates over time and hypomethylation of Alu elements is associated with aging and senescence. Thus, Alu-mediated disruption of nuclear-encoded mitochondrial genes potentially correlates with the aging process and is directly linked with age-related human disease.

Therapeutic intervention of Alu-associated mechanisms operating on nuclear-encoded mitochondrial genes can be achieved by the delivery of targeted antisense oligonucleotides, modification of Alu epigenetic profiles (including flanking nucleotides; e.g., using CRISPR/Cas technology and/or pharmaceutical compounds that alter DNA and/or histone methylation), targeted excision or removal of Alu elements (e.g., using CRISPR/Cas technology), as well as the delivery of agents that alter mitochondrial biogenesis, fusion, or fission. The cited therapeutic approaches are for stabilization of gene transcription and translation (including stabilization of pre-mRNA molecules and mature RNA transcripts) of nuclear-encoded mitochondrial genes that are influenced by the presence of Alu mobile elements.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Prevention and/or Reduction of Alu-Associated Alternative Splicing Events in TOMM40

Therapeutic modification of Alu elements within TOMM40 can be achieved using m RNA antisense oligonucleotides, targeted CRISPR-Cas9 methylation, and/or CRISPR-Cas9 removal of Alu elements in intron 6 and/or intron 9. Within intron 6, CRISPR-Cas9 targeting for targeted methylation and/or excision of Alu elements will be performed between bases 44,894,113 and 44,900,752 on human chromosome 19 (UCSC Genome Browser; assembly GRCh38/hg38). Within intron 9, CRISPR-Cas9 targeting for targeted methylation and/or excision of Alu elements will be performed between bases 44,901,330 and 44,903,034 on human chromosome 19 (UCSC Genome Browser; assembly GRCh38/hg38). Antisense oligonucleotides to reduce alternative Alu-induced TOMM40 isoforms will be designed to dually span both normal exons and Alu sequences within TOMM40 mRNA.

Table 1 illustrates nucleotide sequences of human TOMM40 antisense oligonucleotides targeting TOMM40 intron 9. Therapeutic targets include Alu-associated TOMM40 messenger RNA products. Application of antisense oligonucleotides can mediate alternative splicing events of TOMM40 by binding to and eliminating mRNA products that include retained intron 9 or exons extending into Alu retrotransposon sequences within intron 9.

Table 2 illustrates antisense oligonucleotides targeting TOMM40L (the functional paralog of TOMM40; also identified as TOMM40B) to prevent enrichment of TOMM40L proteins in neuron mitochondrial populations. Therapeutic targets consist of nine TOMM40L exons and application of antisense oligonucleotides can reduce mRNA expression of TOMM40L, thereby stabilizing the central beta-barrel channels of the translocase of outer mitochondrial membrane pore.

Table 3 illustrates nucleotide coordinates for germline insertions of Alu retrotransposons in TOMM40 and APOE on human chromosome 19 (build GRCh38/hg38). Age-related or environmentally induced demethlylation of Alu retrotransposons contributes to alternative splicing events, transcriptional noise, and genomic instability of TOMM40 and/or APOE. Targeted epigenetic modification (including DNA and/or histone modification) of Alu retrotransposons within TOMM40 and/or APOE, and associated intergenic regions, using the CRISPR-Cas9 can result in the stabilization of TOMM40 and/or APOE gene transcription.

CRISPR-Guide sequences for the 5' and 3' modification of the Alu complex flanking the rs10524523 polymorphism within TOMM40 intron 6 are provided in Table 4. CRISPR-Guide sequences for modification of Alu elements within TOMM40 intron 9 are provided in Table 5. The TIMM23/TOMM40 fusion mRNA antisense oligonucleotide therapy target region is set forth in Table 6.

Example 2

Measuring of Alu Methylation Status to Determine Neurodegenerative Disease Risk

DNA and or histone methylation status of Alu elements within or neighboring nuclear-encoded mitochondrial genes including but not limited to genes of the TOMM and TIMM complexes, and neighboring genes implicated in neurodegenerative disease manifestation (e.g. APOE) will be measured using both system-wide whole genome sequencing approaches (e.g., bisulfate-sequencing and/or chromatin immunoprecipitation high-throughput sequencing) and targeted approaches with probes or baits designed to bind to and select regions or genes of interest (relevant coordinates provided in Table 7). Detection of elevated DNA and/or histone demethylation (i.e., enhanced or progressive hypomethylation) of Alu mobile elements within biological samples will be used to measure neurodegenerative disease risk and inform downstream therapeutic approaches. Personalized baseline biomarker/epimarker data generated from biological samples (e.g., peripheral blood, cerebrospinal fluids) across select sampling time points will identify age and/or environment related perturbations to Alu methylation status. The resulting biomarker/epimarker data will be used to measure neurodegenerative disease risk within patients across time.

TABLE 1

TOMM40 Antisense Nucleotide Sequences Targeting TOMM40 Intron 9

| Oligonucleotide ID | Sequence |
|---|---|
| 1 | TTC-CCT-GGT-AAT-GTG-GAG-GC (SEQ ID NO: 1) |
| 2 | GTT-GAG-TCA-CCT-CCT-GCC-TGT-TTC (SEQ ID NO: 2) |

TABLE 2

Antisense oligonucleotides targeting TOMM40L

| Oligonucleotide ID | Sequence |
|---|---|
| 1 | CTG-GCA-AAG-AAA-GCT-GTC-AAA-GAC-C (SEQ ID NO: 3) |
| 2 | CCC-AAT-GTG-TTC-CCC-ATT-TTA-GTC (SEQ ID NO: 4) |
| 3 | GAA-ATG-GCT-GCT-CAG-AAC-CTT-GTT-G (SEQ ID NO: 5) |
| 4 | CCA-GGG-CAC-TCA-TGT-GTA-TAG-TGT-G (SEQ ID NO: 6) |
| 5 | CTG-CTG-TCC-ATA-TCC-CCT-ACC-ACA-G (SEQ ID NO: 7) |
| 6 | TCC-CCA-ATC-AGG-TCA-GGA-TTT-CCT-A (SEQ ID NO: 8) |
| 7 | TGA-TAA-ACT-AGC-TCT-CCT-CCC-AGC-A (SEQ ID NO: 9) |
| 8 | TTT-GCC-CTG-TGG-TAG-TAA-CTT-GCA-T (SEQ ID NO: 10) |
| 9 | TTG-TGT-CTT-GTA-GCC-TTG-TGT-TTG-C (SEQ ID NO: 11) |

TABLE 3

Nucleotide Coordinates for Germline Insertions of Alu Retrotransposons in TOMM40 and APOE on Human Chromosome 19

| Gene Name | Alu Name | Alu Position (GRCh38/hg38) |
|---|---|---|
| TOMM40 | AluSz | chr19: 44894260-44894561 |
| | AluJr | chr19: 44894612-44894727 |
| | AluSz | chr19: 44895530-44895846 |
| | AluJr | chr19: 44896773-44896957 |
| | AluSx | chr19: 44897474-44897632 |
| | AluSp | chr19: 44897633-44897801 |
| | AluJo | chr19: 44897805-44897922 |
| | AluSx | chr19: 44898512-44898837 |
| | AluYc3 | chr19: 44898863-44899150 |
| | AluJr4 | chr19: 44899156-44899322 |
| | AluJb | chr19: 44899323-44899614 |
| | AluJr4 | chr19: 44899615-44899791 |
| | FLAM_A | chr19: 44899792-44899941 |
| | AluY | chr19: 44901461-44901748 |
| | AluSz | chr19: 44901806-44902119 |
| | AluJb | chr19: 44902208-44902495 |
| Intergenic (TOMM40/APOE) | AluSq | chr19: 44905087-44905384 |
| APOE | AluSx | chr19: 44906894-44907181 |
| | AluJb | chr19: 44907316-44907595 |
| | AluJo | chr19: 44908219-44908335 |
| Intergenic (APOE/APOC) | AluSz | chr19: 44909522-44909803 |
| | AluJo | chr19: 44909812-44910028 |
| | AluJo | chr19: 44910030-44910238 |
| | AluSz | chr19: 44910658-44910986 |
| | AluJo | chr19: 44911610-44911765 |
| | AluSx | chr19: 44911766-44912060 |
| | AluJo | chr19: 44912061-44912193 |
| | AluSz | chr19: 44912391-44912697 |
| | AluJo | chr19: 44913318-44913608 |
| Intergenic (APOA2/TOMM40L) | AluSp | chr1: 161224707-161225006 |
| | L1PA12 | chr1: 161224666-161224706 |
| | L1PA12 | chr1: 161225007-161225147 |
| Intergenic TOMM5 | L1MEh | chr9: 37585151-37585614 |
| | AluSz6 | chr9: 37585615-37585901 |
| | L1MEh | chr9: 37585902-37586455 |
| | L1MA3 | chr9: 37586456-37586823 |
| | L1MEh | chr9: 37586824-37587147 |
| | AluSx | chr9: 37587148-37587455 |
| | L1MEh | chr9: 37587456-37587858 |

TABLE 3-continued

Nucleotide Coordinates for Germline Insertions of Alu Retrotransposons in TOMM40 and APOE on Human Chromosome 19

| Gene Name | Alu Name | Alu Position (GRCh38/hg38) |
|---|---|---|
|  | L1MEh | chr9: 37588037-37588121 |
|  | L3 | chr9: 37589034-37589227 |
| TOMM5 | AluJb | chr9: 37589637-37589820 |
|  | L1MB7 | chr9: 37589919-37590109 |
|  | AluJb | chr9: 37590110-37590422 |
|  | L1MB7 | chr9: 37590423-37590637 |
|  | AluSx | chr9: 37591413-37591719 |
|  | AluSx1 | chr9: 37591925-37592157 |
| Intergenic TOMM5 | AluSx | chr9: 37592779-37592942 |
|  | FLAM_C | chr9: 37593232-37593330 |
|  | L1MC5a | chr9: 37593336-37593491 |
|  | AluSx | chr9: 37593508-37593816 |
|  | AluSc8 | chr9: 37594732-37594907 |
|  | AluJo | chr9: 37594908-37595199 |
|  | AluSc8 | chr9: 37595200-37595217 |
|  | FLAM_A | chr9: 37595721-37595840 |
|  | AluSz | chr9: 37597778-37598063 |
| TOMM6 | AluY | chr6: 41788136-41788443 |
|  | AluSg | chr6: 41788754-41789043 |
| Intergenic TOMM7 | MER61B | chr7: 22801905-22802366 |
|  | SVA_D | chr7: 22800210-22801864 |
|  | MER61-int | chr7: 22802383-2280408 |
|  | AluY | chr7: 22804090-22804397 |
|  | MER61-int | chr7: 22804398-22804800 |
|  | AluSx1 | chr7: 22804801-22805096 |
|  | MER61-int | chr7: 22805097-22805988 |
|  | MER61-int | chr7: 22806026-22808138 |
|  | MER61B | chr7: 22808141-22808598 |
|  | L1MD1 | chr7: 22809108-22809499 |
|  | MER4A1 | chr7: 22809500-22809950 |
|  | L1MD1 | chr7: 22809951-22810044 |
|  | FLAM_C | chr7: 22810280-22810410 |
|  | MER4A1_ | chr7: 22810814-2281140 |
|  | AluSc8 | chr7: 22811433-22811736 |
| TOMM7 | AluSg4 | chr7: 22812815-22812861 |
|  | AluSx | chr7: 22814054-22814369 |
|  | AluJo | chr7: 22815414-22815546 |
|  | AluJo | chr7: 22815701-22815830 |
|  | FLAM_C | chr7: 22817412-22817553 |
|  | L1ME4c | chr7: 22817593-22817834 |
|  | AluSz | chr7: 22818278-22818576 |
|  | AluJb | chr7: 22818767-22818909 |
|  | AluSx | chr7: 22819373-22819629 |
|  | AluJr | chr7: 22820055-22820173 |
|  | AluY | chr7: 22821130-22821435 |
|  | AluSz6 | chr7: 22821444-22821768 |
|  | AluSc8 | chr7: 22821855-22822019 |
| Intergenic TOMM7 | FRAM | chr7: 22823762-22823852 |
|  | LTR8 | chr7: 22823856-22824284 |
|  | L1PA16 | chr7: 22824507-22824572 |
|  | LTR8 | chr7: 22824813-22825009 |
|  | FRAM | chr7: 22825011-22825070 |
|  | AluY | chr7: 22825171-22825486 |
|  | L1PA15 | chr7: 22825715-22825935 |
| Intergenic TOMM20 | AluSz | chr1: 235105515-235105807 |
|  | AluSq2 | chr1: 235106045-235106351 |
|  | AluSx3 | chr1: 235106699-235106922 |
|  | AluJr | chr1: 235107858-235108054 |
|  | AluSz6 | chr1: 235108055-235108267 |
|  | AluJr | chr1: 235108268-235108390 |
| TOMM20 | AluJb | chr1: 235112353-235112622 |
|  | L1MC4a | chr1: 235114016-235114174 |
|  | AluYe6 | chr1: 235114433-235114736 |
|  | AluJb | chr1: 235114873-235115176 |
|  | AluSg | chr1: 235115348-235115653 |
|  | LTR40a | chr1: 235115668-235116127 |
|  | AluSx | chr1: 235116128-235116257 |
|  | AluSc | chr1: 235116258-235116549 |
|  | AluSx | chr1: 235116550-235116730 |
|  | AluYm1 | chr1: 235116854-235117164 |
|  | AluSz | chr1: 235117177-235117490 |
|  | AluJr | chr1: 235118538-235118824 |
|  | AluSx1 | chr1: 235120263-235120564 |
|  | AluJb | chr1: 235120700-235120885 |
|  | AluSc | chr1: 235120921-235121218 |
|  | AluSg | chr1: 235123206-235123490 |
|  | AluSx3 | chr1: 235124066-235124367 |
|  | AluYm1 | chr1: 235125204-235125514 |
|  | AluSx3 | chr1: 235125743-235126055 |
|  | AluSx | chr1: 235126148-235126431 |
|  | AluSg | chr1: 235126525-235126820 |
|  | AluSx | chr1: 235127942-235128184 |
| Intergenic TOMM20 | AluSx | chr1: 235129381-235129673 |
|  | MER41C | chr1: 235129781-235130071 |
|  | AluJr | chr1: 235130072-235130365 |
|  | MER41C | chr1: 235130366-235130504 |
|  | AluSx | chr1: 235130505-235130801 |
|  | MER41C | chr1: 235130802-235130929 |
|  | AluJo | chr1: 235131005-235131100 |
|  | LTR9D | chr1: 235131104-235131223 |
|  | ALuSq2 | chr1: 235131229-235131533 |
| Intergenic TOMM20L | AluSx | chr14: 58394215-58394518 |
|  | AluJo | chr14: 58394528-58394668 |
|  | AluSg | chr14: 58394669-58394966 |
|  | AluJo | chr14: 58394967-58395102 |
| TOMM20L | AluSx | chr14: 58396813-58397076 |
|  | AluJo | chr14: 58398891-58399185 |
|  | AluSx | chr14: 58400125-58400449 |
|  | AluSg | chr14: 58400599-58400895 |
|  | AluY | chr14: 58401290-58401584 |
|  | AluSp | chr14: 58402280-58402587 |
|  | AluJr | chr14: 58403076-58403365 |
|  | AluY | chr14: 58403557-58403863 |
|  | AluYa5 | chr14: 58404121-58404428 |
|  | AluSq2 | chr14: 58404969-58405267 |
|  | AluSz6 | chr14: 58405520-58405799 |
|  | AluSq2 | chr14: 58408135-58408437 |
| Intergenic TOMM22 | AluSz | chr22: 38681051-38681347 |
| TOMM22 | AluJb | chr22: 38684804-38685082 |
| TOMM70A | AluSc8 | chr3: 100363124-100363421 |
|  | FAM | chr3: 100364560-100364701 |
|  | AluSz6 | chr3: 100366938-100367232 |
|  | AluSx | chr3: 100368572-100368873 |
|  | AluSq2 | chr3: 100369499-100369800 |
|  | AluSz | chr3: 100371260-100371566 |
|  | L1MB7 | chr3: 100375210-100375739 |
|  | AluJo | chr3: 100375740-100375832 |
|  | L1MB7 | chr3: 100375833-100376369 |
|  | AluJb | chr3: 100376370-100376534 |
|  | L1MB7 | chr3: 100376559-100376760 |
|  | AluSg | chr3: 100377965-100378271 |
|  | AluY | chr3: 100378725-100379006 |
|  | AluJo | chr3: 100379342-100379609 |
|  | AluJb | chr3: 100379624-100379918 |
|  | AluSx | chr3: 100380064-10038036 |
|  | AluSz | chr3: 100383240-100383536 |
|  | AluSz6 | chr3: 100387165-100387446 |
|  | FLAM_A | chr3: 100387470-100387575 |
|  | AluSx1 | chr3: 100389760-100390064 |
|  | AluSz | chr3: 100390546-100390855 |
|  | AluY | chr3: 100390858-100391150 |
|  | AluSx | chr3: 100392417-100392717 |
|  | L1PB3 | chr3: 100392718-100392894 |
|  | AluSp | chr3: 100392895-100393193 |
|  | L1PB3 | chr3: 100393194-100393606 |
|  | AluSz6 | chr3: 100394360-100394434 |
|  | AluSx1 | chr3: 100394507-100394802 |
|  | AluSc8 | chr3: 100395088-100395401 |
|  | AluSx1 | chr3: 100395404-100395572 |
|  | AluSg | chr3: 100397609-100397899 |
|  | AluSx | chr3: 100398106-100398404 |
|  | AluSx | chr3: 100399002-100399294 |
| TOMM34 | FLAM_C | chr20: 44944569-44944699 |
|  | AluSz | chr20: 44945864-44946148 |
|  | AluSz6 | chr20: 44947504-44947801 |
|  | AluSx1 | chr20: 44957197-44957473 |
|  | AluJr | chr20: 44957647-44957942 |

TABLE 3-continued

Nucleotide Coordinates for Germline Insertions of Alu Retrotransposons in TOMM40 and APOE on Human Chromosome 19

| Gene Name | Alu Name | Alu Position (GRCh38/hg38) |
|---|---|---|
| TIMM23 | Alu | chr10: 45993781-45993822 |
| | Alu | chr10: 45993962-45994004 |
| | AluJb | chr10: 45983753-45984043 |
| | AluJb | chr10: 45994462-45994741 |
| | AluJb | chr10: 45996703-45996985 |
| | AluJb | chr10: 45996997-45997224 |
| | AluJb | chr10: 46002189-46002468 |
| | AluJo | chr10: 45978070-45978359 |
| | AluJo | chr10: 45987615-45987925 |
| | AluJo | chr10: 45990429-45990717 |
| | AluJo | chr10: 45997533-45997825 |
| | AluJo | chr10: 46000405-46000519 |
| | AluJr | chr10: 45973629-45973942 |
| | AluJr | chr10: 45991963-45992261 |
| | AluJr | chr10: 45999142-45999334 |
| | AluJr4 | chr10: 45979298-45979606 |
| | AluSc | chr10: 45992552-45992855 |
| | AluSp | chr10: 45991470-45991781 |
| | AluSp | chr10: 45993244-45993491 |
| | AluSq2 | chr10: 45975790-45976015 |
| | AluSx | chr10: 45990116-45990420 |
| | AluSx1 | chr10: 45977749-45978060 |
| | AluSx1 | chr10: 45994060-45994379 |
| | AluSx1 | chr10: 45998831-45999133 |
| | AluSx3 | chr10: 45980924-45981238 |
| | AluSz | chr10: 46002810-46003112 |
| | AluSz6 | chr10: 45976328-45976627 |
| | AluSz6 | chr10: 45993491-45993555 |
| | AluSz6 | chr10: 45993617-45993657 |
| | AluY | chr10: 45996079-45996372 |
| TIMM17 | AluJb | chr1: 201958420-201958713 |
| | AluJb | chr1: 201967556-201967835 |
| | AluJo | chr1: 201961569-201961691 |
| | AluJo | chr1: 201963843-201964090 |
| | AluSc8 | chr1: 201964605-201964947 |
| | AluSg | chr1: 201959373-201959683 |
| | AluSp | chr1: 201957856-201958148 |
| | AluSq | chr1: 201963075-201963374 |
| | AluSq2 | chr1: 201961061-201961366 |
| | AluSx | chr1: 201960756-201961047 |
| | AluSx1 | chr1: 201960117-201960411 |
| | AluSx1 | chr1: 201964950-201965223 |
| | AluSx1 | chr1: 201968382-201968673 |
| | AluSx3 | chr1: 201959205-20195937 |
| | AluSx4 | chr1: 201956679-201956975 |
| | AluSx4 | chr1: 201967995-201968293 |
| | AluSz | chr1: 201966560-201966847 |
| | AluSz6 | chr1: 201966217-201966381 |
| | AluY | chr1: 201959692-201960028 |
| | AluY | chr1: 201962341-201962648 |
| | FLAM_A | chr1: 201966391-201966498 |
| TIMM50 | AluJb | chr19: 39487267-39487445 |
| | AluJb | chr19: 39487758-39487891 |
| | AluJr | chr19: 39484253-39484416 |
| | AluJr | chr19: 39490377-39490688 |
| | AluSc | chr19: 39484951-39485261 |
| | AluSp | chr19: 39490740-39491045 |
| | AluSx | chr19: 39483846-39484152 |
| | AluSx3 | chr19: 39487445-39487758 |
| | AluY | chr19: 39482375-39482676 |
| | FLAM_C | chr19: 39484763-39484905 |

TABLE 4

CRISPR Guide Sequences for Modification of TOMM40 Alu Complex within Intron 6

(SEQ ID NO: 12) CCTAGGAGATTGCTCGATCGTGG (SEQ ID NO: 13) AGGAGATTGCTCGATCGTGGTGG

TABLE 4-continued

CRISPR Guide Sequences for Modification of TOMM40 Alu Complex within Intron 6

(SEQ ID NO: 14) CACGATCGAGCAATCTCCTAGGG (SEQ ID NO: 15) CCACGATCGAGCAATCTCCTAGG (SEQ ID NO: 16) TCTGTGTGCCCTCAGTCTCGTGG (SEQ ID NO: 17) GTTGGGGGCCACGAGACTGAGGG (SEQ ID NO: 18) AATCTCCTAGGGTGCAGCCCTGG (SEQ ID NO: 19) ATGACCAGAGGGGCAGACTAGGG (SEQ ID NO: 20) CCCAGACCAAGATGACCAGAGGG (SEQ ID NO: 21) GGTTGGGGGCCACGAGACTGAGG (SEQ ID NO: 22) CCCTCTGGTCATCTTGGTCTGGG (SEQ ID NO: 23) TCCCAGACCAAGATGACCAGAGG (SEQ ID NO: 24) TGACCAGAGGGGCAGACTAGGGG (SEQ ID NO: 25) CCAGACCAAGATGACCAGAGGGG (SEQ ID NO: 26) GTCTGCCCCTCTGGTCATCTTGG (SEQ ID NO: 27) GATGACCAGAGGGGCAGACTAGG (SEQ ID NO: 28) GGGCCCCTAGTCTGCCCCTCTGG (SEQ ID NO: 29) CCCCTCTGGTCATCTTGGTCTGG (SEQ ID NO: 30) GCCCTGGAGAGGAAGACACGTGG (SEQ ID NO: 31) TCCACGTGTCTTCCTCTCCAGGG (SEQ ID NO: 32) GAGAGGAAGACACGTGGAGAAGG (SEQ ID NO: 33) CTCCACGTGTCTTCCTCTCCAGG (SEQ ID NO: 34) CAAGCACTCCCTACGGTGGAGGG (SEQ ID NO: 35) GCAAGCACTCCCTACGGTGGAGG (SEQ ID NO: 36) TTTCGAGCCTAGCAGGGTACAGG (SEQ ID NO: 37) TCAGCAAGCACTCCCTACGGTGG (SEQ ID NO: 38) TGGTGTCTTTCGAGCCTAGCAGG (SEQ ID NO: 39) TCCTGTGTCCCTCCACCGTAGGG (SEQ ID NO: 40) TCCCTACGGTGGAGGGACACAGG (SEQ ID NO: 41) TTCCTGTGTCCCTCCACCGTAGG (SEQ ID NO: 42) TGTTCAGCAAGCACTCCCTACGG (SEQ ID NO: 43) GGGACACAGGAACGCAGACTTGG (SEQ ID NO: 44) GGATGGAGATGGATTCACTTTGG (SEQ ID NO: 45) GGGCTGCCTTTTCAAGCCTCAGG (SEQ ID NO: 46) ACAAGAGAACTGCCACCTTTGGG (SEQ ID NO: 47) AACAAGAGAACTGCCACCTTTGG (SEQ ID NO: 48) TTATAGGGCCAGAAGAATTGGGG (SEQ ID NO: 49) TTTGTGGCCTGTACCCTGCTAGG (SEQ ID NO: 50) GGCTTGAAAAGGCAGCCCAAAGG (SEQ ID NO: 51) TTTTATAGGGCCAGAAGAATTGGG (SEQ ID NO: 52) CTCCATCCTGAGGCTTGAAAAGG

TABLE 4-continued

CRISPR Guide Sequences for Modification of TOMM40 Alu Complex within Intron 6

(SEQ ID NO: 53) TAGGGCCAGAAGAATTGGGGAGG (SEQ ID NO: 54) GGTGTCTTTCGAGCCTAGCAGGG (SEQ ID NO: 55) CTCTTCCTCCCCAATTCTTCTGG (SEQ ID NO: 56) TGCCTTTTCAAGCCTCAGGATGG (SEQ ID NO: 57) TTTTATAGGGCCAGAAGAATTGG (SEQ ID NO: 58) GCCCTATAAAATCACATTTGTGG (SEQ ID NO: 59) GGCCACAAATGTGATTTTATAGG

TABLE 5

CRISPR Guide Sequences for Modification of TOMM40 Alu Complex within Intron 9

(SEQ ID NO: 60) GGTTCCCCTACGCGGGAAACAGG (SEQ ID NO: 61) AGGTCTCGGTTCCCCTACGCGGG (SEQ ID NO: 62) AAGGTCTCGGTTCCCCTACGCGG (SEQ ID NO: 63) TCCTGCCTGTTTCCCGCGTAGGG (SEQ ID NO: 64) CCTGCCTGTTTCCCGCGTAGGGG (SEQ ID NO: 65) CTCCTGCCTGTTTCCCGCGTAGG (SEQ ID NO: 66) CCCCTACGCGGGAAACAGGCAGG (SEQ ID NO: 67) CTGTGGGCCTCCACATTACCAGG (SEQ ID NO: 68) TGTGGGCCTCCACATTACCAGGG (SEQ ID NO: 69) CTGGTAATGTGGAGGCCCACAGG (SEQ ID NO: 70) GTGGATGTGTGGGCCACCACAGG (SEQ ID NO: 71) ACAGTGTGCTGCCACCCTGTGGG (SEQ ID NO: 72) AGTGTTCCCTGGTAATGTGGAGG (SEQ ID NO: 73) CACTTGTTAAAAGGTAGGTGGGG (SEQ ID NO: 74) ACAAGTGTTCCCTGGTAATGTGG (SEQ ID NO: 75) GGAGGTGACTCAACTCTGAGTGG (SEQ ID NO: 76) GGGAACACTTGTTAAAAGGTAGG (SEQ ID NO: 77) ACACTTGTTAAAAGGTAGGTGGG (SEQ ID NO: 78) GTGTGGGCCACCACAGGTGCTGG (SEQ ID NO: 79) TCAACTCTGAGTGGATGTGTGGG (SEQ ID NO: 80) TGGTAATGTGGAGGCCCACAGGG (SEQ ID NO: 81) CTCAACTCTGAGTGGATGTGTGG (SEQ ID NO: 82) CTACGCGGGAAACAGGCAGGAGG (SEQ ID NO: 83) GACAGTGTGCTGCCACCCTGTGG (SEQ ID NO: 84) ACCAGGGAACACTTGTTAAAAGG (SEQ ID NO: 85) TAATGTGGAGGCCCACAGGGTGG (SEQ ID NO: 86) AACACTTGTTAAAAGGTAGGTGG

TABLE 5-continued

CRISPR Guide Sequences for Modification of TOMM40 Alu Complex within Intron 9

(SEQ ID NO: 87) CCTCTACTATGTTTTATGCTTGG (SEQ ID NO: 88) CCAAGCATAAAACATAGTAGAGG (SEQ ID NO: 89) CAAGCATAAAACATAGTAGAGGG (SEQ ID NO: 90) AATCTGGTGGAGCATCTGATGGG (SEQ ID NO: 91) GATGGGTGTTTGGGCCAAGCTGG (SEQ ID NO: 92) GGATGGACAAAGCTCCAGCTTGG (SEQ ID NO: 93) GGAGCATCTGATGGGTGTTTGGG (SEQ ID NO: 94) TGGAGCATCTGATGGGTGTTTGG (SEQ ID NO: 95) AAATCTGGTGGAGCATCTGATGG (SEQ ID NO: 96) CCCCATTCATCTTACGTTAGTGG (SEQ ID NO: 97) TAACGTAAGATGAATGGGGCAGG (SEQ ID NO: 98) TCCACTAACGTAAGATGAATGGG (SEQ ID NO: 99) CCACTAACGTAAGATGAATGGGG (SEQ ID NO: 100) TCTTACGTTAGTGGAAACTGAGG (SEQ ID NO: 101) AGTTGTGACCTTGAAACCTCTGG (SEQ ID NO: 102) TTCCACTAACGTAAGATGAATGG (SEQ ID NO: 103) GTGTGCCTGAGATGAGGTTCTGG (SEQ ID NO: 104) GAAGACTTAAGACTGGACATTGG (SEQ ID NO: 105) GACAGGGCTGGTCACCGCTGTGG (SEQ ID NO: 106) TGTCCAGTCTTAAGTCTTCTTGG (SEQ ID NO: 107) AGATGAATGGGGCAGGCTCGAGG (SEQ ID NO: 108) AGCCAGGGTAGAAGGCACTTTGG (SEQ ID NO: 109) TAAATCCAGAACCTCATCTCAGG (SEQ ID NO: 110) TATCCAAGAAGACTTAAGACTGG (SEQ ID NO: 111) GAACCTCATCTCAGGCACACTGG (SEQ ID NO: 112) TAAGTCTTCTTGGATATCTGTGG (SEQ ID NO: 113) CGACCAGTGTGCCTGAGATGAGG (SEQ ID NO: 114) AAGACTTAAGACTGGACATTGGG (SEQ ID NO: 115) TGAGGCTTCCAGAGGTTTCAAGG (SEQ ID NO: 116) TATCTGTGGCTCACAGATTTTGG (SEQ ID NO: 117) AGCCTCCTGCTGAGCACTGCTGG (SEQ ID NO: 118) ATCTGTGGCTCACAGATTTTGGG

TABLE 6

TIMM23/TOMM40 Fusion mRNA Antisense Oligonucleotide Therapy Target Region

AGAGACACGATATTGCACGATCTGTTATTACTACCCCATGAAACTAGAAA

ACACTATACAACCAGAAATCAGAGATCGAAGCTTGTTAGTACTATATCAA

CCAAGTCCATTTCATTAAATGATCCAAAAATGTAATGTTGCACTGTATTC

TABLE 6-continued

TIMM23/TOMM40 Fusion mRNA Antisense Oligonucleotide Therapy Target Region

CAAATAAAGGGTATAACAAACCAAAGTTATACTCCAAAAAAAAAAAAAA

AAAAAAGTACTCCTGGGTATACCACTGCTTAAAGCAGCTGGTATCAAACG

GCAGAGTACACTGTCAGCCGTCCACCCCTGGGGAACCCAGACGTCCTCGT

TGGGTTCAGGATCCTCGTAGCCCACTACCTCCAGAGCATTCACGCCTTGC

CGGCCCTGGGTGGAGAGCGGTCTACACCGGTCGGCTGGAGAGGAAGGGCA

CATGTCAGTCTCTAGCGAGGAATACACACCTTGAAAACTGGTTGCAACGG

TAACGTTGGGCCA (SEQ ID NO: 119)

TABLE 7

Human Genome Coordinates (build GRch38/hg38) for Alu Biomarker/Epimarker Analyses to Determine Neurodegenerative Disease Risk

| Gene | Human Chromosome | Nucleotide Positions |
| --- | --- | --- |
| TOMM5 | 9 | 37,588,413-37,592,642 |
| TOMM6 | 6 | 41,787,662-41,789,898 |
| TOMM7 | 7 | 22,812,632-22,822,851 |
| TOMM20 | 1 | 235,109,336-235,128,936 |
| TOMM22 | 22 | 38,681,948-38,685,421 |
| TOMM40 | 19 | 44,891,220-44,903,689 |
| TOMM70 | 3 | 100,363,431-100,401,398 |
| TOMM40L | 1 | 161,226,003-161,230,607 |
| TIMM17 | 1 | 201,955,491-201,970,661 |
| TIMM23 | 10 | 45,972,449-46,003,734 |
| TIMM50 | 19 | 39,480,412-39,490,888 |
| APOE | 19 | 44,905,754-44,909,393 |

What is claimed is:

1. A method of or treating a disease or disorder associated with at least one translocase of outer mitochondrial membrane complex (TOMM), translocase of inner mitochondrial membrane complex (TIMM), or apolipoprotein E (APOE) isoform, said method comprising administering to a subject a therapeutically effective dose of a composition comprising at least one antisense oligonucleotide, wherein the antisense oligonucleotide is selected from SEQ ID NOs:1-11, thereby treating the disease or disorder.

2. The method of claim 1, wherein the disease or disorder is a neurological disorder.

3. The method of claim 1, wherein the TOMM, TIMM, or APOE isoform polynucleotide is an Alu element-induced isoform.

4. The method of claim 1, wherein the TOMM, TIMM, or APOE isoform polynucleotide is an Alu element-induced TOMM40 isoform.

* * * * *

SEQUENCE LISTING

<160> NUMBER OF SEQ ID NOS: 121

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ttccctggta atgtggaggc                                              20

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gttgagtcac ctcctgcctg tttc                                         24

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctggcaaaga aagctgtcaa agacc                                        25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cccaatgtgt tccccatttt agtc                                         24

```
<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gaaatggctg ctcagaacct tgttg                                          25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccagggcact catgtgtata gtgtg                                          25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctgctgtcca tatcccctac cacag                                          25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tccccaatca ggtcaggatt tccta                                          25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tgataaacta gctctcctcc cagca                                          25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tttgccctgt ggtagtaact tgcat                                          25

<210> SEQ ID NO 11
```

<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttgtgtcttg tagccttgtg tttgc                                        25

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cctaggagat tgctcgatcg tgg                                          23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aggagattgc tcgatcgtgg tgg                                          23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cacgatcgag caatctccta ggg                                          23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ccacgatcga gcaatctcct agg                                          23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tctgtgtgcc ctcagtctcg tgg                                          23

<210> SEQ ID NO 17
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gttgggggcc acgagactga ggg                                              23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aatctcctag ggtgcagccc tgg                                              23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
atgaccagag gggcagacta ggg                                              23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cccagaccaa gatgaccaga ggg                                              23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggttgggggc cacgagactg agg                                              23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ccctctggtc atcttggtct ggg                                              23

<210> SEQ ID NO 23
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 23
tcccagacca agatgaccag agg                                              23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tgaccagagg ggcagactag ggg                                              23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ccagaccaag atgaccagag ggg                                              23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gtctgcccct ctggtcatct tgg                                              23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gatgaccaga ggggcagact agg                                              23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gggcccctag tctgcccctc tgg                                              23

<210> SEQ ID NO 29
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 29
cccctctggt catcttggtc tgg                                              23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gccctggaga ggaagacacg tgg                                              23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tccacgtgtc ttcctctcca ggg                                              23

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gagaggaaga cacgtggaga agg                                              23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ctccacgtgt cttcctctcc agg                                              23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
caagcactcc ctacggtgga ggg                                              23

<210> SEQ ID NO 35
<211> LENGTH: 23
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 35
gcaagcactc cctacggtgg agg                                           23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tttcgagcct agcagggtac agg                                           23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tcagcaagca ctccctacgg tgg                                           23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tggtgtcttt cgagcctagc agg                                           23

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tcctgtgtcc ctccaccgta ggg                                           23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tccctacggt ggagggacac agg                                           23

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
ttcctgtgtc cctccaccgt agg                                        23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tgttcagcaa gcactcccta cgg                                        23

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gggacacagg aacgcagact tgg                                        23

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ggatggagat ggattcactt tgg                                        23

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gggctgcctt ttcaagcctc agg                                        23

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
acaagagaac tgccaccttt ggg                                        23

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aacaagagaa ctgccacctt tgg					23

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttatagggcc agaagaattg ggg					23

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tttgtggcct gtaccctgct agg					23

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ggcttgaaaa ggcagcccaa agg					23

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tttatagggc cagaagaatt ggg					23

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ctccatcctg aggcttgaaa agg					23

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tagggccaga agaattgggg agg                                              23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ggtgtctttc gagcctagca ggg                                              23

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ctcttcctcc ccaattcttc tgg                                              23

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tgccttttca agcctcagga tgg                                              23

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ttttataggg ccagaagaat tgg                                              23

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gccctataaa atcacatttg tgg                                              23

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ggccacaaat gtgattttat agg     23

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60 ggttcccta cgcgggaaac agg     23

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
aggtctcggt tcccctacgc ggg     23

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
aaggtctcgg ttccctacg cgg     23

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tcctgcctgt ttcccgcgta ggg     23

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cctgcctgtt tcccgcgtag ggg     23

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ctcctgcctg tttcccgcgt agg                                              23

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cccctacgcg ggaaacaggc agg                                              23

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ctgtgggcct ccacattacc agg                                              23

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tgtgggcctc cacattacca ggg                                              23

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ctggtaatgt ggaggcccac agg                                              23

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gtggatgtgt gggccaccac agg                                              23

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
acagtgtgct gccaccctgt ggg                                              23

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
agtgttccct ggtaatgtgg agg                                           23

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
cacttgttaa aaggtaggtg ggg                                           23

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
acaagtgttc cctggtaatg tgg                                           23

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ggaggtgact caactctgag tgg                                           23

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gggaacactt gttaaaaggt agg                                           23

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
acacttgtta aaaggtaggt ggg                                           23

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gtgtgggcca ccacaggtgc tgg                                              23

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tcaactctga gtggatgtgt ggg                                              23

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tggtaatgtg gaggcccaca ggg                                              23

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ctcaactctg agtggatgtg tgg                                              23

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ctacgcggga aacaggcagg agg                                              23

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gacagtgtgc tgccaccctg tgg                                              23

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
accagggaac acttgttaaa agg                                           23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
taatgtggag gcccacaggg tgg                                           23

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
aacacttgtt aaaaggtagg tgg                                           23

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cctctactat gttttatgct tgg                                           23

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ccaagcataa aacatagtag agg                                           23

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
caagcataaa acatagtaga ggg                                           23

<210> SEQ ID NO 90

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
aatctggtgg agcatctgat ggg                                           23

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gatgggtgtt tgggccaagc tgg                                           23

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ggatggacaa agctccagct tgg                                           23

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ggagcatctg atgggtgttt ggg                                           23

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tggagcatct gatgggtgtt tgg                                           23

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
aaatctggtg gagcatctga tgg                                           23

<210> SEQ ID NO 96
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ccccattcat cttacgttag tgg                                             23

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
taacgtaaga tgaatggggc agg                                             23

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tccactaacg taagatgaat ggg                                             23

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ccactaacgt aagatgaatg ggg                                             23

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tcttacgtta gtggaaactg agg                                             23

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
agttgtgacc ttgaaacctc tgg                                             23

<210> SEQ ID NO 102
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 102
ttccactaac gtaagatgaa tgg                                                23

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gtgtgcctga gatgaggttc tgg                                                23

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gaagacttaa gactggacat tgg                                                23

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gacagggctg gtcaccgctg tgg                                                23

<210> SEQ ID NO 106
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tgtccagtct taagtcttct tgg                                                23

<210> SEQ ID NO 107
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
agatgaatgg ggcaggctcg agg                                                23

<210> SEQ ID NO 108
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 108
agccagggta gaaggcactt tgg                                              23

<210> SEQ ID NO 109
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
taaatccaga acctcatctc agg                                              23

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
tatccaagaa gacttaagac tgg                                              23

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gaacctcatc tcaggcacac tgg                                              23

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
taagtcttct tggatatctg tgg                                              23

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
cgaccagtgt gcctgagatg agg                                              23

<210> SEQ ID NO 114
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 114
aagacttaag actggacatt ggg                                              23

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tgaggcttcc agaggtttca agg                                              23

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
tatctgtggc tcacagattt tgg                                              23

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
agcctcctgc tgagcactgc tgg                                              23

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
atctgtggct cacagatttt ggg                                              23

<210> SEQ ID NO 119
<211> LENGTH: 463
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
agagacacga tattgcacga tctgttatta ctaccccatg aaactagaaa acactataca      60
accagaaatc agagatcgaa gcttgttagt actatatcaa ccaagtccat ttcattaaat     120
gatccaaaaa tgtaatgttg cactgtattc caaataaagg gtataacaaa ccaaagttat     180
actccaaaaa aaaaaaaaaa aaaaaagtac tcctgggtat accactgctt aaagcagctg     240
gtatcaaacg gcagagtaca ctgtcagccg tccacccctg gggaacccag acgtcctcgt     300
```

```
tgggttcagg atcctcgtag cccactacct ccagagcatt cacgccttgc cggccctggg    360
tggagagcgg tctacaccgg tcggctggag aggaagggca catgtcagtc tctagcgagg    420
aatacacacc ttgaaaactg gttgcaacgg taacgttggg cca                     463
```

<210> SEQ ID NO 120
<211> LENGTH: 361
<212> TYPE: PRT
<213> ORGANISM: Homo sapiens

<400> SEQUENCE: 120

```
Met Gly Asn Val Leu Ala Ala Ser Ser Pro Pro Ala Gly Pro Pro Pro
1               5                   10                  15

Pro Pro Ala Pro Ala Leu Val Gly Leu Pro Pro Pro Pro Ser Pro
        20                  25                  30

Pro Gly Phe Thr Leu Pro Pro Leu Gly Gly Ser Leu Gly Ala Gly Thr
        35                  40                  45

Ser Thr Ser Arg Ser Ser Glu Arg Thr Pro Gly Ala Ala Thr Ala Ser
    50                  55                  60

Ala Ser Gly Ala Ala Glu Asp Gly Ala Cys Gly Cys Leu Pro Asn Pro
65                  70                  75                  80

Gly Thr Phe Glu Glu Cys His Arg Lys Cys Lys Glu Leu Phe Pro Ile
                85                  90                  95

Gln Met Glu Gly Val Lys Leu Thr Val Asn Lys Gly Leu Ser Asn His
            100                 105                 110

Phe Gln Val Asn His Thr Val Ala Leu Ser Thr Ile Gly Glu Ser Asn
        115                 120                 125

Tyr His Phe Gly Val Thr Tyr Val Gly Thr Lys Gln Leu Ser Pro Thr
    130                 135                 140

Glu Ala Phe Pro Val Leu Val Gly Asp Met Asp Asn Ser Gly Ser Leu
145                 150                 155                 160

Asn Ala Gln Val Ile His Gln Leu Gly Pro Gly Leu Arg Ser Lys Met
                165                 170                 175

Ala Ile Gln Thr Gln Gln Ser Lys Phe Val Asn Trp Gln Val Asp Gly
            180                 185                 190

Glu Tyr Arg Gly Ser Asp Phe Thr Ala Ala Val Thr Leu Gly Asn Pro
        195                 200                 205

Asp Val Leu Val Gly Ser Gly Ile Leu Val Ala His Tyr Leu Gln Ser
    210                 215                 220

Ile Thr Pro Cys Leu Ala Leu Gly Gly Glu Leu Val Tyr His Arg Arg
225                 230                 235                 240

Pro Gly Glu Glu Gly Thr Val Met Ser Leu Ala Gly Lys Tyr Thr Leu
                245                 250                 255

Asn Asn Trp Leu Ala Thr Val Thr Leu Gly Gln Ala Gly Met His Ala
            260                 265                 270

Thr Tyr Tyr His Lys Ala Ser Asp Gln Leu Gln Val Gly Val Glu Phe
        275                 280                 285

Glu Ala Ser Thr Arg Met Gln Asp Thr Ser Val Ser Phe Gly Tyr Gln
    290                 295                 300

Leu Asp Leu Pro Lys Ala Asn Leu Leu Phe Lys Gly Ser Val Asp Ser
305                 310                 315                 320

Asn Trp Ile Val Gly Ala Thr Leu Glu Lys Lys Leu Pro Pro Leu Pro
                325                 330                 335

Leu Thr Leu Ala Leu Gly Ala Phe Leu Asn His Arg Lys Asn Lys Phe
```

```
                    340                 345                 350
Gln Cys Gly Phe Gly Leu Thr Ile Gly
        355                 360

<210> SEQ ID NO 121
<211> LENGTH: 335
<212> TYPE: PRT
<213> ORGANISM: Homo sapiens

<400> SEQUENCE: 121

Met Gly Asn Val Leu Ala Ala Ser Ser Pro Ala Gly Pro Pro Pro
1               5                   10                  15

Pro Pro Ala Pro Ala Leu Val Gly Leu Pro Pro Pro Pro Ser Pro
                20                  25                  30

Pro Gly Phe Thr Leu Pro Pro Leu Gly Gly Ser Leu Gly Ala Gly Thr
            35                  40                      45

Ser Thr Ser Arg Ser Ser Glu Arg Thr Pro Gly Ala Ala Thr Ala Ser
    50                  55                      60

Ala Ser Gly Ala Ala Glu Asp Gly Ala Cys Gly Cys Leu Pro Asn Pro
65                  70                  75                  80

Gly Thr Phe Glu Glu Cys His Arg Lys Cys Lys Glu Leu Phe Pro Ile
                85                  90                  95

Gln Met Glu Gly Val Lys Leu Thr Val Asn Lys Gly Leu Ser Asn His
                100                 105                 110

Phe Gln Val Asn His Thr Val Ala Leu Ser Thr Ile Gly Glu Ser Asn
            115                 120                 125

Tyr His Phe Gly Val Thr Tyr Val Gly Thr Lys Gln Leu Ser Pro Thr
    130                 135                 140

Glu Ala Phe Pro Val Leu Val Gly Asp Met Asp Asn Ser Gly Ser Leu
145                 150                 155                 160

Asn Ala Gln Val Ile His Gln Leu Gly Pro Gly Leu Arg Ser Lys Met
                165                 170                 175

Ala Ile Gln Thr Gln Gln Ser Lys Phe Val Asn Trp Gln Val Asp Gly
                180                 185                 190

Glu Tyr Arg Gly Ser Asp Phe Thr Ala Ala Val Thr Leu Gly Asn Pro
    195                 200                 205

Asp Val Leu Val Gly Ser Gly Ile Leu Val Ala His Tyr Leu Gln Ser
210                 215                 220

Ile Thr Pro Cys Leu Ala Leu Gly Gly Glu Leu Val Tyr His Arg Arg
225                 230                 235                 240

Pro Gly Glu Glu Gly Thr Val Met Ser Leu Ala Gly Lys Tyr Thr Leu
                245                 250                 255

Asn Asn Trp Leu Ala Thr Val Thr Leu Gly Gln Ala Gly Met His Ala
                260                 265                 270

Thr Tyr Tyr His Lys Ala Ser Asp Gln Leu Gln Val Gly Val Glu Phe
    275                 280                 285

Glu Ala Ser Thr Arg Met Gln Asp Thr Ser Val Ser Phe Gly Tyr Gln
290                 295                 300

Leu Asp Leu Pro Lys Ala Asn Leu Leu Phe Lys Gly Ala Gly Gly Gln
305                 310                 315                 320

Cys Ala Ala Thr Leu Trp Ala Ser Thr Leu Pro Gly Asn Thr Cys
                325                 330                 335
```